(12) United States Patent
Huebner

(10) Patent No.: US 7,918,892 B2
(45) Date of Patent: *Apr. 5, 2011

(54) SHOULDER PROSTHESIS

(75) Inventor: Randall J. Huebner, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 339 days.

This patent is subject to a terminal disclaimer.

(21) Appl. No.: 11/986,307

(22) Filed: Nov. 19, 2007

(65) Prior Publication Data

US 2008/0306600 A1    Dec. 11, 2008

Related U.S. Application Data

(63) Continuation of application No. 10/321,282, filed on Dec. 16, 2002, now Pat. No. 7,297,163, which is a continuation of application No. 09/507,564, filed on Feb. 18, 2000, now Pat. No. 6,494,913, which is a continuation-in-part of application No. 09/191,928, filed on Nov. 13, 1998, now Pat. No. 6,102,953, which is a continuation-in-part of application No. 09/165,475, filed on Oct. 2, 1998, now Pat. No. 6,193,758, and a continuation-in-part of application No. 09/040,504, filed on Mar. 17, 1998, now Pat. No. 5,961,555.

(51) Int. Cl.
    *A61F 2/40*    (2006.01)
(52) U.S. Cl. .................................... 623/19.11
(58) Field of Classification Search .... 623/19.11–19.14, 623/20.35, 20.36, 22.4–22.43, 23.15, 20.14, 623/20.11, 23.11, 20.13, 20.12; 606/95, 606/86–89, 62–68, 96–99, 102, 104, 79, 606/80, 84, 86 R
See application file for complete search history.

(56) References Cited

U.S. PATENT DOCUMENTS

| | | |
|---|---|---|
| 2,531,734 A | 11/1950 | Hopkins |
| 2,570,465 A | 10/1951 | Lundholm |
| 2,682,265 A | 6/1954 | Collison |
| 2,719,522 A | 10/1955 | Hudack |
| 2,765,787 A | 10/1956 | Pellet |
| 2,781,758 A | 2/1957 | Chevalier |
| 2,785,673 A | 3/1957 | Anderson |
| 3,064,645 A | 11/1962 | Ficat et al. |
| 3,067,740 A | 12/1962 | Haboush |
| 3,102,536 A | 9/1963 | Rose et al. |
| 3,334,624 A | 8/1967 | Schneider et al. |
| 3,506,982 A | 4/1970 | Steffee |
| 3,554,192 A | 1/1971 | Isberner |
| 3,658,056 A | 4/1972 | Huggler et al. |

(Continued)

FOREIGN PATENT DOCUMENTS

CH    619132    9/1980

(Continued)

OTHER PUBLICATIONS

A Biomechanical Analysis of Four Humeral Fracture Fixation Systems, Zimmerman et al., *Journal of Orthopaedic Trauma*, vol. 8, No. 3, pp. 233-239, 1994.

(Continued)

*Primary Examiner* — Alvin J. Stewart
(74) *Attorney, Agent, or Firm* — Kolisch Hartwell, P.C.

(57) ABSTRACT

A system and method for installing a shoulder prosthesis. The method includes removing the original humeral head and shaping the proximal end of the humerus with one or more implements to prepare the humerus to receive the shoulder prosthesis.

11 Claims, 16 Drawing Sheets

U.S. PATENT DOCUMENTS

| | | |
|---|---|---|
| 3,670,724 A | 6/1972 | Bosacco |
| 3,694,820 A | 10/1972 | Scales et al. |
| 3,708,805 A | 1/1973 | Scales et al. |
| 3,763,855 A | 10/1973 | McAtee |
| 3,765,034 A | 10/1973 | Johnston |
| 3,781,918 A | 1/1974 | Mathys |
| 3,782,373 A | 1/1974 | Smythe |
| 3,803,641 A | 4/1974 | Golyakhovsky |
| 3,806,957 A | 4/1974 | Shersher |
| 3,814,089 A | 6/1974 | Deyerle |
| 3,818,512 A | 6/1974 | Shersher |
| 3,859,669 A | 1/1975 | Shersher |
| 3,863,273 A | 2/1975 | Averill |
| 3,874,003 A | 4/1975 | Moser et al. |
| 3,879,767 A | 4/1975 | Stubstad |
| 3,892,232 A | 7/1975 | Neufeld |
| 3,906,550 A | 9/1975 | Rostoker et al. |
| 3,916,451 A | 11/1975 | Buechel et al. |
| 3,918,441 A | 11/1975 | Getscher |
| 3,974,527 A | 8/1976 | Shersher |
| 3,977,398 A | 8/1976 | Burstein |
| 3,979,778 A | 9/1976 | Stroot |
| 3,987,499 A | 10/1976 | Scharbach et al. |
| 4,004,300 A | 1/1977 | English |
| 4,030,143 A | 6/1977 | Elloy et al. |
| 4,040,131 A | 8/1977 | Gristina |
| 4,042,980 A | 8/1977 | Swanson et al. |
| 4,045,825 A | 9/1977 | Stroot |
| 4,051,559 A | 10/1977 | Pifferi |
| 4,115,875 A | 9/1978 | Rambert et al. |
| 4,129,902 A | 12/1978 | Harmon |
| 4,194,250 A | 3/1980 | Walker |
| 4,199,824 A | 4/1980 | Niederer |
| 4,205,400 A | 6/1980 | Shen et al. |
| 4,212,294 A | 7/1980 | Murphy |
| 4,242,758 A | 1/1981 | Amis et al. |
| 4,261,062 A | 4/1981 | Amstutz et al. |
| 4,287,617 A | 9/1981 | Tornier |
| 4,293,963 A | 10/1981 | Gold et al. |
| 4,332,037 A | 6/1982 | Esformes et al. |
| 4,357,716 A | 11/1982 | Brown |
| 4,378,607 A | 4/1983 | Wadsworth |
| 4,383,337 A | 5/1983 | Volz et al. |
| 4,404,691 A | 9/1983 | Buning et al. |
| 4,404,692 A | 9/1983 | Eftekhar |
| 4,406,023 A | 9/1983 | Harris |
| 4,430,761 A | 2/1984 | Niederer et al. |
| 4,459,708 A | 7/1984 | Buttazzoni |
| 4,474,177 A | 10/1984 | Whiteside |
| 4,487,203 A | 12/1984 | Androphy |
| 4,488,319 A | 12/1984 | Von Recum |
| 4,524,467 A | 6/1985 | DeCarlo, Jr. |
| 4,532,660 A | 8/1985 | Field |
| 4,538,306 A | 9/1985 | Dorre et al. |
| 4,550,450 A | 11/1985 | Kinnett |
| 4,574,794 A | 3/1986 | Cooke et al. |
| 4,578,081 A | 3/1986 | Harder et al. |
| 4,608,055 A | 8/1986 | Morrey et al. |
| 4,624,674 A | 11/1986 | Pappas et al. |
| 4,628,923 A | 12/1986 | Medoff |
| 4,645,506 A | 2/1987 | Link |
| 4,655,778 A | 4/1987 | Koeneman |
| 4,667,664 A | 5/1987 | Taylor et al. |
| 4,676,797 A | 6/1987 | Anapliotis et al. |
| 4,686,971 A | 8/1987 | Harris et al. |
| 4,693,723 A | 9/1987 | Gabard |
| 4,693,724 A | 9/1987 | Rhenter et al. |
| 4,697,585 A | 10/1987 | Williams |
| 4,698,063 A | 10/1987 | Link et al. |
| 4,703,751 A | 11/1987 | Pohl |
| 4,718,414 A | 1/1988 | Saunders et al. |
| 4,736,737 A | 4/1988 | Fargie et al. |
| 4,795,468 A | 1/1989 | Hodorek et al. |
| 4,822,370 A | 4/1989 | Schelhas |
| 4,840,632 A | 6/1989 | Kampner |
| 4,842,606 A | 6/1989 | Kranz et al. |
| 4,846,841 A | 7/1989 | Oh |
| 4,865,605 A | 9/1989 | Dines et al. |
| 4,865,609 A | 9/1989 | Roche |
| 4,875,475 A | 10/1989 | Comte et al. |
| 4,892,546 A | 1/1990 | Kotz et al. |
| 4,893,619 A | 1/1990 | Dale et al. |
| 4,895,572 A | 1/1990 | Chernoff |
| 4,903,691 A | 2/1990 | Heinl |
| 4,904,266 A | 2/1990 | Barber |
| 4,905,679 A | 3/1990 | Morgan |
| 4,908,032 A | 3/1990 | Keller |
| 4,913,137 A | 4/1990 | Azer et al. |
| 4,919,669 A | 4/1990 | Lannelongue |
| 4,919,670 A | 4/1990 | Dale et al. |
| 4,932,974 A | 6/1990 | Pappas et al. |
| 4,936,854 A | 6/1990 | Swanson |
| 4,952,213 A | 8/1990 | Bowman et al. |
| 4,959,066 A | 9/1990 | Dunn et al. |
| 4,963,155 A | 10/1990 | Lazzeri et al. |
| 4,964,865 A | 10/1990 | Burkhead et al. |
| 4,986,833 A | 1/1991 | Worland |
| 4,988,351 A | 1/1991 | Paulos et al. |
| 4,995,883 A | 2/1991 | Demane et al. |
| 5,002,545 A | 3/1991 | Whiteside et al. |
| 5,002,580 A | 3/1991 | Noble et al. |
| 5,002,581 A | 3/1991 | Paxson et al. |
| 5,007,933 A | 4/1991 | Sidebotham et al. |
| 5,030,234 A | 7/1991 | Pappas et al. |
| 5,030,237 A | 7/1991 | Sorbie et al. |
| 5,032,130 A | 7/1991 | Schelhas et al. |
| 5,032,132 A | 7/1991 | Matsen, III et al. |
| 5,047,061 A | 9/1991 | Brown |
| 5,061,287 A | 10/1991 | Feiler |
| 5,071,420 A | 12/1991 | Paulos et al. |
| 5,074,879 A | 12/1991 | Pappas et al. |
| 5,078,746 A | 1/1992 | Garner |
| 5,080,676 A | 1/1992 | May |
| 5,080,685 A | 1/1992 | Bolesky et al. |
| 5,100,407 A | 3/1992 | Conrad et al. |
| 5,108,396 A | 4/1992 | Lackey et al. |
| 5,108,437 A | 4/1992 | Kenna |
| 5,108,452 A | 4/1992 | Fallin et al. |
| 5,116,379 A | 5/1992 | McLardy-Smith |
| 5,133,760 A | 7/1992 | Petersen et al. |
| 5,135,529 A | 8/1992 | Paxson et al. |
| 5,154,717 A | 10/1992 | Matsen, III et al. |
| 5,163,961 A | 11/1992 | Harwin |
| 5,169,401 A | 12/1992 | Lester et al. |
| 5,171,288 A | 12/1992 | Mikhail et al. |
| 5,171,324 A | 12/1992 | Campana et al. |
| 5,181,928 A | 1/1993 | Bolesky et al. |
| 5,207,682 A | 5/1993 | Cripe |
| 5,236,432 A | 8/1993 | Matsen, III et al. |
| 5,248,313 A | 9/1993 | Greene et al. |
| 5,250,055 A | 10/1993 | Moore et al. |
| 5,261,915 A | 11/1993 | Durlacher et al. |
| 5,282,865 A | 2/1994 | Dong |
| 5,286,260 A | 2/1994 | Bolesky et al. |
| 5,314,479 A | 5/1994 | Rockwood, Jr. et al. |
| 5,314,486 A | 5/1994 | Zang et al. |
| 5,336,268 A | 8/1994 | Rispeter |
| 5,342,363 A | 8/1994 | Richelsoph |
| 5,342,366 A | 8/1994 | Whiteside et al. |
| 5,344,458 A | 9/1994 | Bonutti |
| 5,358,526 A | 10/1994 | Tornier |
| 5,364,398 A | 11/1994 | Chapman et al. |
| 5,370,706 A | 12/1994 | Bolesky et al. |
| 5,387,239 A | 2/1995 | Bianco et al. |
| 5,389,107 A | 2/1995 | Nassar et al. |
| 5,403,319 A | 4/1995 | Matsen, III et al. |
| 5,405,403 A | 4/1995 | Mikhail |
| 5,433,718 A | 7/1995 | Brinker |
| 5,433,720 A | 7/1995 | Faccioli et al. |
| 5,472,444 A | 12/1995 | Huebner et al. |
| 5,480,402 A | 1/1996 | Kim |
| 5,489,309 A | 2/1996 | Lackey et al. |
| 5,507,817 A | 4/1996 | Craig et al. |
| 5,507,818 A | 4/1996 | McLaughlin |
| 5,507,830 A | 4/1996 | DeMane et al. |
| 5,509,935 A | 4/1996 | Fosco et al. |
| 5,514,143 A | 5/1996 | Bonutti et al. |

| | | |
|---|---|---|
| 5,549,609 A | 8/1996 | Frankel et al. |
| 5,549,682 A | 8/1996 | Roy |
| 5,569,263 A | 10/1996 | Hein |
| 5,571,203 A | 11/1996 | Masini |
| 5,580,352 A | 12/1996 | Sekel |
| 5,586,985 A | 12/1996 | Putnam et al. |
| 5,591,233 A | 1/1997 | Kelman et al. |
| 5,645,548 A | 7/1997 | Augsburger |
| 5,645,607 A | 7/1997 | Hickey |
| 5,649,930 A | 7/1997 | Kertzner |
| 5,658,340 A | 8/1997 | Muller et al. |
| 5,658,349 A | 8/1997 | Brooks et al. |
| 5,658,352 A | 8/1997 | Draenert |
| 5,662,651 A | 9/1997 | Tornier et al. |
| 5,665,090 A | 9/1997 | Rockwood et al. |
| 5,690,635 A | 11/1997 | Matsen, III et al. |
| 5,702,447 A | 12/1997 | Walch et al. |
| 5,702,457 A | 12/1997 | Walch et al. |
| 5,702,460 A | 12/1997 | Carls et al. |
| 5,702,469 A | 12/1997 | Whipple et al. |
| 5,702,472 A | 12/1997 | Huebner |
| 5,702,486 A | 12/1997 | Craig et al. |
| 5,713,901 A | 2/1998 | Tock |
| 5,725,595 A | 3/1998 | Gustilo |
| 5,728,161 A | 3/1998 | Camino et al. |
| 5,741,335 A | 4/1998 | Gerber et al. |
| 5,776,194 A | 7/1998 | Mikol et al. |
| 5,776,204 A | 7/1998 | Noble et al. |
| 5,779,705 A | 7/1998 | Matthews |
| 5,779,709 A | 7/1998 | Harris, Jr. et al. |
| 5,782,923 A | 7/1998 | Engelbrecht et al. |
| 5,788,700 A | 8/1998 | Morawa et al. |
| 5,792,143 A | 8/1998 | Samuelson et al. |
| 5,800,560 A | 9/1998 | Draenert |
| 5,814,047 A | 9/1998 | Emilio et al. |
| 5,860,982 A | 1/1999 | Ro et al. |
| 5,879,395 A | 3/1999 | Tornier et al. |
| 5,885,297 A | 3/1999 | Matsen, III |
| 5,888,245 A | 3/1999 | Meulink et al. |
| 5,910,171 A | 6/1999 | Kummer et al. |
| 5,951,564 A | 9/1999 | Schroder et al. |
| 5,961,555 A | 10/1999 | Huebner |
| 5,976,149 A | 11/1999 | Masini |
| 5,989,259 A | 11/1999 | Penenberg et al. |
| 6,015,437 A | 1/2000 | Stossel |
| 6,019,761 A | 2/2000 | Gustilo |
| 6,033,439 A | 3/2000 | Camino et al. |
| 6,045,582 A | 4/2000 | Prybyla |
| 6,102,953 A | 8/2000 | Huebner |
| 6,110,179 A | 8/2000 | Flivik et al. |
| 6,120,507 A | 9/2000 | Allard et al. |
| 6,120,542 A | 9/2000 | Camino et al. |
| 6,120,544 A | 9/2000 | Grundei et al. |
| 6,123,708 A | 9/2000 | Kilpela et al. |
| 6,156,069 A | 12/2000 | Amstutz |
| 6,165,177 A | 12/2000 | Wilson et al. |
| 6,165,224 A | 12/2000 | Tornier |
| 6,168,627 B1 | 1/2001 | Huebner |
| 6,168,628 B1 | 1/2001 | Huebner |
| 6,171,341 B1 | 1/2001 | Boileau et al. |
| 6,193,758 B1 | 2/2001 | Huebner |
| 6,197,062 B1 | 3/2001 | Fenlin |
| 6,197,063 B1 | 3/2001 | Dews |
| 6,206,925 B1 | 3/2001 | Tornier |
| 6,217,616 B1 | 4/2001 | Ogilvie |
| 6,228,119 B1 | 5/2001 | Ondrla et al. |
| 6,228,120 B1 | 5/2001 | Leonard et al. |
| 6,267,785 B1 | 7/2001 | Masini |
| 6,277,123 B1 | 8/2001 | Maroney et al. |
| 6,283,999 B1 | 9/2001 | Rockwood, Jr. |
| 6,336,941 B1 | 1/2002 | Subba Rao et al. |
| 6,379,391 B1 | 4/2002 | Masini |
| 6,395,004 B1 | 5/2002 | Dye et al. |
| 6,398,812 B1 | 6/2002 | Masini |
| 6,402,753 B1 | 6/2002 | Cole et al. |
| 6,494,913 B1 | 12/2002 | Huebner |
| 6,508,820 B2 | 1/2003 | Bales |
| 6,517,541 B1 | 2/2003 | Sesic |
| 6,533,788 B1 | 3/2003 | Orbay |
| 6,579,294 B2 | 6/2003 | Robioneck |
| 6,652,529 B2 | 11/2003 | Swanson |
| 6,692,496 B1 | 2/2004 | Wardlaw |
| 6,706,046 B2 | 3/2004 | Orbay et al. |
| 6,719,799 B1 | 4/2004 | Kropf |
| 6,730,090 B2 | 5/2004 | Orbay et al. |
| 6,793,659 B2 | 9/2004 | Putnam |
| 2001/0001120 A1 | 5/2001 | Masini |
| 2001/0008981 A1 | 7/2001 | Masini |
| 2001/0049561 A1 | 12/2001 | Dews et al. |
| 2001/0053935 A1 | 12/2001 | Hartdegen et al. |
| 2002/0042654 A1 | 4/2002 | Masini |
| 2002/0095217 A1 | 7/2002 | Masini |
| 2002/0128720 A1 | 9/2002 | Masini |
| 2002/0151982 A1 | 10/2002 | Masini |

FOREIGN PATENT DOCUMENTS

| | | |
|---|---|---|
| DE | 2015324 | 11/1971 |
| DE | 2246274 | 3/1974 |
| DE | 2400650 | 7/1974 |
| DE | 3023354 | 4/1981 |
| DE | 3329978 | 3/1985 |
| DE | 3415934 | 10/1985 |
| DE | 4320086 | 12/1994 |
| DE | 4331282 | 3/1995 |
| DE | 19548154 | 6/1997 |
| DE | 29805703 | 10/1998 |
| DE | 19858889 | 6/2000 |
| EP | 0 000 549 | 2/1979 |
| EP | 0 017 743 | 6/1982 |
| EP | 0 145 939 | 8/1985 |
| EP | 0 163 212 | 12/1985 |
| EP | 0 190 981 | 8/1986 |
| EP | 0 201 407 | 11/1986 |
| EP | 0 098 224 | 1/1987 |
| EP | 0 118 778 | 6/1987 |
| EP | 0 132 284 | 4/1988 |
| EP | 0 145 666 | 6/1988 |
| EP | 0 163 121 | 8/1988 |
| EP | 0 198 163 | 7/1989 |
| EP | 0 339 530 | 11/1989 |
| EP | 0 278 807 | 4/1992 |
| EP | 0 243 298 | 3/1993 |
| EP | 0 501 207 | 12/1993 |
| EP | 0 581 667 | 2/1994 |
| EP | 0 607 749 | 7/1994 |
| EP | 0 617 934 | 10/1994 |
| EP | 0 634 154 | 1/1995 |
| EP | 0 393 608 | 6/1995 |
| EP | 0 622 062 | 6/1997 |
| EP | 0 611 225 | 9/1997 |
| EP | 0 679 375 | 9/1998 |
| EP | 0 639 359 | 3/1999 |
| EP | 0 712 617 | 9/1999 |
| EP | 0 776 636 | 9/2000 |
| EP | 1 064 890 | 1/2001 |
| EP | 1 080 702 | 3/2001 |
| EP | 0 715 836 | 10/2001 |
| EP | 1 143 867 | 7/2002 |
| EP | 0 664 108 | 8/2002 |
| EP | 1 013 246 | 10/2003 |
| FR | 2225141 | 4/1974 |
| FR | 2378505 | 8/1978 |
| FR | 2567019 | 1/1986 |
| FR | 2574283 | 6/1986 |
| FR | 2576793 | 8/1986 |
| FR | 2578162 | 9/1986 |
| FR | 2579454 | 10/1986 |
| FR | 2606273 | 5/1988 |
| FR | 2619502 | 2/1989 |
| FR | 2634371 | 1/1990 |
| FR | 2652498 | 4/1991 |
| FR | 2663838 | 1/1992 |
| FR | 2664809 | 1/1992 |
| FR | 2670108 | 6/1992 |
| FR | 2683142 | 5/1993 |
| FR | 2689756 | 10/1993 |
| FR | 2689757 | 10/1993 |
| FR | 2689758 | 10/1993 |

| | | |
|---|---|---|
| FR | 2695313 | 3/1994 |
| FR | 2699400 | 6/1994 |
| FR | 2704747 | 11/1994 |
| FR | 2705558 | 12/1994 |
| FR | 2737107 | 1/1997 |
| FR | 2755847 | 5/1998 |
| FR | 2770128 | 4/1999 |
| GB | 0 747 876 | 4/1956 |
| GB | 1 443 470 | 7/1976 |
| GB | 1 521 679 | 8/1978 |
| GB | 1 531 487 | 11/1978 |
| GB | 1 537 479 | 12/1978 |
| GB | 1 593 440 | 7/1981 |
| GB | 2 070 939 | 9/1981 |
| GB | 2 094 639 | 9/1982 |
| GB | 2 223 172 | 4/1990 |
| GB | 2 297 257 | 7/1996 |
| GB | 2 334 890 | 9/1999 |
| JP | 63-73951 | 4/1988 |
| JP | 3-500978 | 3/1991 |
| JP | 7-501001 | 2/1995 |
| JP | 7-313524 | 12/1995 |
| JP | 2003-517337 | 5/2003 |
| PL | 171292 | 3/1997 |
| RU | 2119307 | 9/1998 |
| SU | 1 279 629 | 12/1986 |
| SU | 1 734 727 | 5/1992 |
| WO | WO 83/02555 | 8/1983 |
| WO | WO 91/18559 | 12/1991 |
| WO | WO 93/09733 | 5/1993 |
| WO | WO 94/04085 | 3/1994 |
| WO | WO 94/15551 | 7/1994 |
| WO | WO 94/29701 | 12/1994 |
| WO | WO 96/17553 | 6/1996 |
| WO | WO 96/41597 | 12/1996 |
| WO | WO 97/27828 | 8/1997 |
| WO | WO 98/07393 | 2/1998 |
| WO | WO 98/15241 | 4/1998 |
| WO | WO 98/46172 | 10/1998 |
| WO | WO 00/36984 | 6/2000 |
| WO | WO 00/41653 | 7/2000 |
| WO | WO 01/19264 | 3/2001 |
| WO | WO 01/19268 | 3/2001 |
| WO | WO 02/17822 | 3/2002 |

OTHER PUBLICATIONS

A Biomechanical Comparison of Intramedullary Nailing Systems for the Humerus, Dalton et al., *Journal of Orthopaedic Trauma*, vol. 7, No. 4, pp. 367-374, 1993.
A Locking Nail for Fractures of the Humerus, Habernek et al., *The Journal of Bone and Joint Surgery*, vol. 73-B, No. 4, pp. 651-653, Jul. 1991.
A Review of the Use of Modularity in Total Shoulder Arthroplasty, Zuckerman et al., *Modularity of Orthopedic Implants*, pp. 5-18, 1997.
Acumed "Elbows & Shoulders Above the Rest" Polarus Modular Shoulder, Acumed LLC, Feb. 23, 2001.
Acumed Great Toe System information page, Acumed, Inc., Jun. 1994.
Acute Hemiarthroplasty After Proximal Humerus Fracture in Old Patients, Wretenberg et al., *Acta. Orthop. Scand.*, vol. 68, No. 2, pp. 121-123, 1997.
Acute Prosthetic Replacement for Severe Fractures of the Proximal Humerus, Hawkins et al., *Clinical Orthopaedics and Related Research*, No. 289, pp. 156-160, 1993.
Adaptability and Modularity of Shoulder Prostheses, Boileau et al., reprint from *Mautrise Orthopedique*, Sep. 1993.
Aequalis Fracture Jig Shoulder Prosthesis brochure, Tornier, Jun. 1995.
*An Analysis of 122 Failed Shoulder Arthroplasties*, Duckworth et al., Societe Internationale de Chirurgie Orthopedique et de Traumatologie, 21st Trianhual World Congress, Apr. 18-23, 1999 (abstract only).
Anchor Peg Glenoid design rationale and surgical technique, DePuy Orthopaedics, Inc., 2002.
Anthropometric Study of Normal Glenohumeral Relationships, McPherson et al., *J. Shoulder Elbow Surg.*, vol. 6, No. 2, pp. 105-112, Mar./Apr. 1997.
*Anthropometric Study of the Gleno Humeral Joint*, Maki et al., 22nd Annual ORS, Jan. 28-30, 1976.
Arthroplasty and Acute Shoulder Trauma, Compito et al., *Clinical Orthopaedics and Related Research*, No. 307, pp. 27-36, 1994.
Articular Replacement for the Humeral Head, Neer II et al., *The Journal of Bone and Joint Surgery*, vol. 37-A, No. 2, pp. 215-228, Apr. 1955.
Assessing Morse Taper Function: The Relationship Between Impaction Force, Disassembly Force, and Design Variables, Schmidt et al., *Modularity of Orthopedic Implants*, pp. 114-126, 1997.
Basic Biomechanics of the Skeletal System, Frankel, pp. 236-240, 1980.
Beredjiklian, et al. "Prosthetic Radial Head Components and Proximal Radial Morphology: A Mismatch," *Journal of Shoulder Elbow Surgery*, pp. 471-475, Sep./Oct. 1999.
Bigliani, Proximal Humerus Fractures, *Master Techniques in Orthopaedic Surgery*, pp. 43-71, © Jan. 2002.
Biologic Fixation of a Press-Fit Titanium Hip Joint Endoprosthesis, Zewymuller et al., *Clinical Orthopaedics*, vol. 235, pp. 195-205, Oct. 1988.
Biomechanical Analysis of Stability and Fixation Strength of Total Shoulder Prostheses, Fukuda et al., *Orthopedics*, vol. 11, No. 1, pp. 141-149, Jan. 1988.
Biomechanical Comparison of Antegrade and Retrograde Nailing of Humeral Shaft Fracture, Lin et al., *Clinical Orthopaedics and Related Research*, No. 351, pp. 203-213, 1998.
Biomechanical Comparison of Intramedullary and Percutaneous Pin Fixation for Proximal Humeral Fracture Fixation, Wheeler et al., Orthopaedic Research Society 42 Annual Meeting, Feb. 19-22, 1996.
Biomechanical Effects of Malposition of Tuberosity Fragments on the Humeral Prosthetic Reconstruction for Four-Part Proximal Humerus Fractures, Frankle et al., *J. Shoulder Elbow Surg.*, vol. 10, No. 4, pp. 321-326, Jul./Aug. 2001.
Biomechanics of Intramedullary Nailing, Bechtold et al., *The Journal of Trauma*, pp. 89-101, 1996.
Biomechanics of Total Shoulder Arthroplasty: A Preoperative and Postoperative Analysis, Friedman, *Seminars in Arthroplasty*, vol. 6, No. 4, pp. 222-232, Oct. 1995.
Bio-Modular Total Shoulder brochure, Biomet, Inc., © 1990.
Bio-Modular/Bi-Polar Shoulder Arthroplasty brochure, Biomet Inc., 1997.
Bohl, et al., "Fracture of a Silastic Radial-Head Prosthesis: Diagnosis and Localization of fragments by Xerography," *The Journal of Bone and Joint Surgery*, vol. 63-A, pp. 1482-1483, 1981.
Boileau et al., *Shoulder Arthroplasty for Proximal Humeral Fractures: Problems and Solutions*, Paper Presented at the 16th Annual Meeting on Arthroscopic Surgery of the Shoulder, Oceanside, California, pp. 92-109, Jun. 1999.
Boileau, et al., "The Three-Dimensional Geometry of the Proximal Humerus," *The Journal of Bone and Joint Surgery*, vol. 79-B, No. 5, pp. 857-865, Sep. 1997.
Buechel-Pappas Total Shoulder System instructions, Oct. 1991.
Burkheard, Jr., "The Intermedics Select Shoulder System," Intermedic Orthopedics, © 1992.
Capanna et al., "A Humeral Modular Prostheses for Bone Tumour Surgery: A Study of 56 cases," *International Orthopaedics*, vol. 10, No. 4, pp. 231-238, 1986.
Caputo, et al., "The Nonarticulating Portion of the Radial Head: Anatomic and Clinical Correlations for Internal Fixation," *The Journal of Head Surgery*, vol. 23A, No. 6, pp. 1082-1089, Nov. 1998.
Cam, et al., "Silicone Rubber Replacement of the Severely Fractured Radial Head," *Clinical Orthopaedics and Related Research*, No. 209, pp. 259-269, Aug. 1986.
Cement Versus Noncement: Humerus, Knetsche et al., *Operative Techniques in Orthopaedics*, vol. 4, No. 4, pp. 210-217, Oct. 1994.
Cementless Total Shoulder Arthroplasty: Preliminary Experience with Thirteen Cases, Faludi et al., *Orthopedics*, vol. 6, No. 9, pp. 431-437, Apr. 1983.
Characterization of Solid Products of Corrosion Generated by Modular-Head Femoral Stems of Different Designs and Materials, Urban et al., *Modularity of Orthopedic Implants*, pp. 33-59, 1997.
Charnley Flanged Prosthesis advertisement, Cintor Orthopaedic Division, 1980.

Closed Kuntscher Nailing of Humeral Shaft Fractures, Vander Griend et al., *Journal of Trauma*, vol. 25, No. 12, pp. 1167-1169, Dec. 1985.

Cofield[2] Total Shoulder System brochure, Smith & Nephew Richards Inc., Nov. 1996.

Cook, et al., "The Wear Characteristics of the Canine Acetabulum Against Different Femoral Prostheses," *The Journal of Bone and Joint Surgery*, vol. 71-B, No. 2, pp. 189-197, Mar. 1989.

Diaphyseal Fractures of the Humerus, Zagorski et al., *The Journal of Bone and Joint Surgery* vol. 70-A, No. 4, pp. 607-610, Apr. 1988.

Displaced Three- and Four-Part Proximal Humerus Fractures: Evaluation and Management, Naranja et al., *Journal of the American Academy of Orthopaedic Surgeons*, Vo. 8, No. 6, pp. 373-382, Nov./Dec. 2000.

Dissociation of Modular Humeral Head Components: A Biomechanical and Implant Retrieval Study, Blevins et al., *J. Shoulder Elbow Surg.*, vol. 6, No. 2, pp. 113-124, Mar./Apr. 1997.

Effect of Humeral Head Component Size on Hemiarthroplasty Translations and Rotations, Blevins et al., *J. Shoulder Elbow Surg.*, vol. 7, No. 6, pp. 591-598, Nov./Dec. 1998.

Fenlin Total Shoulder Brochure, Zimmer, Inc., © 1998.

Fenlin, Jr. et al., "Modular Total Shoulder Replacement: Design Rationale, Indications, and Results," *Clinical Orthopaedics and Related Research*, No. 307, pp. 37-46, © 1994.

Fixation of Three-Part Proximal Humeral Fractures: A Biomechanical Evaluation, Ruch et al., *J. Orthop. Trauma*, vol. 14, No. 1, pp. 36-40, 2000.

Four Part Humeral Fracture Repair description, DePuy, Inc., 1995.

Four-Part Valgus Impacted Fractures of the Proximal Humerus, Jakob et al., *Journal of Bone and Joint Surgery*, vol. 73-B, No. 2, pp. 295-298, Mar. 1991.

Fretting Corrosion Fatigue Study of Modular Joints in Total Hip Replacements by Accelerated In Vitro Testing, Bhambri et al., *Modularity of Orthopedic Implants*, pp. 146-156, 1997.

Fretting Corrosion Mechanisms at Modular Implant Interfaces, *Modularity of Orthopedic Implants*, pp. 211-223, 1997.

Geometric Analysis of Commonly Used Prosthetic Systems for Proximal Humeral Replacement, Pearl et al., *The Journal of Bone and Joint Surgery*, vol. 81-A, No. 5, pp. 660-671, May 1999.

Global Advantage CTA Humeral Head design rationale and surgical technique, DePuy Orthopaedics, Inc., 2000.

Global Advantage Shoulder Arthroplasty System design rationale, DePuy Orthopaedics, Inc., 2000.

Global Advantage Shoulder Arthroplasty System surgical technique, DePuy Orthopaedics, Inc., 2000.

Global Fx Shoulder Fracture System, Advertisement pages, *Orthopedics*, vol. 22, No. 9, Sep. 1999.

*Global Fx Shoulder Fracture System*, Surgical Technique, DePuy Orthopaedics, 1999.

Global Total Shoulder Arthroplasty System brochure, 1995.

Global Total Shoulder Arthroplasty System design rationale and surgical technique, DePuy Orthopaedics, Inc., 1994.

Global Total Shoulder Arthroplasty System product rationale and surgical technique, DePuy Orthopaedics, Inc., 1999.

Global Total Shoulder Arthroplasty System, DePuy Inc., © 1992.

Globalfx Shoulder Fracture System brochure, DePuy Orthopaedics, Inc., 1999.

Globalfx Shoulder Fracture System design rationale, DePuy Orthopaedics, Inc., 2002.

Gray's Anatomy Descriptive and Surgical, Gray, Henry, pp. 1, 123, 126, 1995.

Great Toe System (GTS) surgical technique, Acumed, Inc., Sep. 15, 1994.

Gupta, et al., "Biomechanical and Computer Analysis of Radial Head Prostheses," *Journal of Shoulder Elbow Surgery*, pp. 37-48, Jan./Feb. 1997.

Harness, et al., "Loss of Fixation of the Volar Lunate Facet Fragment in Fractures of the Distal Part of the Radius," *The Journal of Bone and Joint Surgery*, vol. 86-A, No. 9, pp. 1900-1908, Sep. 2004.

Hemiarthroplasty for the Treatment of Proximal Humeral Fractures, Schlegel et al., *Operative Techniques in Orthopaedics*, vol. 4, No. 1, pp. 21-25, Jan. 1994.

Hemiarthroplasty in Rotator Cuff Tear Arthropathy, Frieman et al., *The Department of Orthopaedic Surgery*, 1994.

Hemiarthroplasty in Rotator Cuff-Deficient Shoulders, Williams et al., *J. Shoulder Elbow Surg.*, vol. 5, No. 5, pp. 362-367, Sep./Oct. 1996.

Hemiarthroplasty in the Treatment of Communited Intraarticular Fractures of the Proximal Humerus, Dimakopoulos et al., *Clinical Orthopaedics and Related Research*, No. 341, pp. 7-11, 1997.

Hemiarthroplasty Techniques for Proximal Humerus Fractures, Dines et al., *Complications in Orthopedics*, pp. 25-31, Jan./Feb. 1991.

Hotchkiss, Robert N., "Displaced Fractures of the Radial Head; Internal Fixation or Excision?" *The Journal of American Academy of Orthopaedic Surgeons*, vol. 5, No. 1, pp. 1-10, Jan./Feb. 1997.

Howmedica Your Orthopaedic Resource 1992 Product Catalog, Codman & Shurleff, Inc., 1992.

Humeral Fracture Following Shoulder Arthroplasty, Kligman et al., *Orthopedics*, No. 22, No. 5, pp. 511-512, May 1999.

Humeral Head Replacement for Acute Proximal Humerus Fracture: A Multicenter Prospective Functional Outcomes Study, Green et al., *J. Shoulder Eblow Surg.*, vol. 8, No. 2, p. 190, 1999 (abstract only).

*Humeral Head Replacement for Four-Part Fractures and Fracture-Dislocations*, Green et al.,pp. 13-19, 1994.

Humeral Head Replacement for Proximal Humeral Fractures, Levine et al., *Orthopedics*, vol. 21, No. 1, pp. 68-73, Jan. 1998.

Humeral Shaft Fractures: Intramedullary Nailing, Riemer, *Master Techniques in Orthopaedic Surgery*, 81-94, 1998.

Iannotti et al., "Total Shoulder Arthroplast: Factors Influencing Prosthetic Sizing," *University of Pennsylvania Medical Center*, 1994.

Interlocking Nail Fixation for Humeral Shaft Fractures, Kellam, published by: *Department of Orthopaedic Surgery*, Carolinas Medical Center, 1991.

Intermedics Orthopedics Select Shoulder System advertisement, Intermedics Orthopedics, Inc., 1993.

Intermedics Orthopedics Select Shoulder System brochure, Intermedics Orthopedics, Inc., Feb. 1994.

Internal Fixation of Three-Part Proximal Humeral Fractures, Schlegel et al., *Operative Techniques in Orthopaedics*, vol. 4, No. 1, pp. 9-12, Jan. 1994.

Intramedullary Fixation of Complicated Fractures of the Humeral Shaft, Watanabe, *Clinical Orthopaedics and Related Research*, No. 292, pp. 255-263, 1993.

Intramedullary Nailing of the Humerus, Riemer, *The Journal of Trauma*, pp. 241-263, 1996.

Investigations on the Galvanic Corrosion of Multialloy Total Hip Prostheses, Lucas et al., *Journal of Biomedical Materials Research*, vol. 15, pp. 731-747, 1981.

King, et al. "An Anthropometric Study of the Radial Head; Implications in the Design of a Prosthesis," *The Journal of Arthroplasty*, vol. 16, No. 1, pp. 112-116, 2001.

Knight, et al., "Primary Replacement of the Fractured Radial Head with a Metal Prosthesis," *The Journal of Bone and Joint Surgery*, vol. 75-B, No. 4, pp. 572-576, Jul. 1993.

Limits Imposed on Glenohumeral Motion by Joint Geometry, Jobe et al., *J. Shoulder Elbow Surg.*, vol. 4, No. 4, pp. 281-285, Jul./Aug. 1995.

Locked Intramedullary Nailing of Humeral Shaft Fractures, Ingman et al., *Journal of Bone and Joint Surgery*, vol. 26-B, No. 1, pp. 23-29, Jan. 1994.

Locked Nailing of Femoral Fractures, Court-Brown et al., *The Journal of Trauma*, pp. 161-181, 1996.

Locked Nailing of Humeral Shaft Fractures, Robinson et al., *Journal of Bone and Joint Surgery*, vol. 74-B, No. 4, pp. 558-562, Jul. 1992.

Matsen, III et al., Global Total Shoulder Arthroplasty System, DePuy®, © 1992.

Measuring Outcomes in Shoulder Arthroplasty, Kuhn et al., *Seminars in Arthroplasty*, vol. 6, No. 4, pp. 245-264, Oct. 1995.

Modular Shoulder Arthroplasty, Gartsman et al., *J. Shoulder Elbow Surg.*, vol. 6, No. 4, pp. 333-339, Jul./Aug. 1997.

Modular Shoulder Hemiarthroplasty, Coleman et al., *Orthopedic*, vol. 6, No. 1, pp. 35-38, 2000.

Moeckel et al., "Modular Hemiarthroplasty for Fractures of the Proximal Part of the Humerus," *The Journal of Bone and Joint Surgery.*, vol. 74-A, No. 6, pp. 884-889. Jul. 1992.

Morphologic Study of the Glenoid in Primary Glenohumeral Osteoarthritis, Walch et al., *The Journal of Arthroplasty.*, vol. 14, No. 6, pp. 756-760, Sep. 1999.

Moskal et al., *A Radiographic Analysis of 122 Failed Shoulder Arthroplasties*, Paper No. 137, Abstract only, Presented at the 66th Annual Meeting of the American Academy of Orthopaedic Surgeons, Anaheim, California, Feb. 1999.

*New Product Rollout Package: Global Fx THE Shoulder Fracture System*, DePuy Orthopaedics, Sep. 22, 1999.

*Noncemented Hemiarthroplasty for Three- and Four-Part Fractures of the Proximal Humerus*, Peterson et al., American Academy of Orthopaedic Surgeons, 66th Annual Meeting Proceedings, Feb. 4-8, 1999 (abstract only).

Observations on the Function of the Shoulder Joint, Inman et al., *The Journal of Bone and Joint Surgery*, vol. 26, No. 1, pp. 1-30, Jan. 1944.

Operating Room Technique, Atkinson et al., page number unknown, 2001.

Operative Treatment of Two-Part, Displaced Surgical Neck Fractures of the Proximal Humerus, Flatow et al., *Operative Techniques in Orthopaedics*, vol. 4, No. 1, pp. 2-8, Jan. 1994.

Osteonics Shoulder System X-ray analysis templates, Osteonics Corp., 1996.

Outcome After Hemiarthroplasty for Three- and Four-Part Fractures of the Proximal Humerus, Zyto et al., *J. Shoulder Elbow Surg.*, Vo. 7, No. 2, pp. 85-89, Mar./Apr. 1998.

Pearl et al., "Retroversion of the Proximal Humerus in Relationship to Prosthetic Replacement Arthroplasty," *J. Shoulder Elbow Surg.*, vol. 4, Jul./Aug. 1995.

Periprosthetic Fractures in Total Shoulder Replacement, Krakauer et al., *The Department of Orthopedic Surgery*, 1994.

*Polarus Modular Shoulder System* surgical technique, Acumed, LLC, May 7, 2002.

*Polarus Modular Shoulder System* technical monograph, Acumed, Inc., Feb. 14, 2002.

*Polarus Modular Shoulder System*, Surgical Technique, Acumed, Inc., Sep. 22, 2000.

*Polarus Modular Shoulder System*, Technical Monograph, Acumed, Inc., 2001.

Polarus Plus surgical technique, Acumed, Inc., Dec. 1, 1995.

*Polarus*, Surgical Technique, Acumed, Inc., Nov. 17, 1999.

Polarus: The First Total Humeral Fixation System brochure, Acumed, Inc., Aug. 19, 1996.

Pribyl et al., "The Effect of the Radial Head and Prosthetic Radial Head Replacement on Resisting Valgus Stress at the Elbow," *Orthopedics*, vol. 9, No. 5, pp. 723-726, May 1986.

Prosthetic Design Considerations in Total Shoulder Arthroplasty, Flatow, *Seminars in Arthroplasty*, vol. 6, No. 4, pp. 233-244, Oct. 1995.

Proximal Humeral Fractures: Arthroplasty, Bigliani, *Master Techniques in Orthopaedic Surgery*, pp. 47-71, 1998.

Proximal Humerus Fractures, Bigliani, *The Shoulder: Operative Technique*, pp. 43-71, 1998.

*Restoration of Glenohumeral Anatomy Following Total Shoulder Arthroplasty*, Friedman, Societe Internationale de Chirurgie Orthopedique et de Traumatologie, 21st Trianhual World Congress, Apr. 18-23, 1999 (abstract only).

*Results After Shoulder Arthroplasty for Rheumatoid Arthritis and Osteoarthritis*, Krepler et al., Societe Internationale de Chirurgie Orthopedique et de Traumatologie, 21st Trianhual World Congress, Apr. 18-23, 1999 (abstract only).

*Results of the Aequalis Shoulder Prosthesis in Chronic Cases*, Walch et al., Arthroscopic Surgery of the Shoulder 16th Annual San Diego Meeting, pp. 110-113, Jun. 23-26, 1999.

Retroversion of the Humeral Head in the Normal Shoulder and its Relationship to the Normal Range of Motion, Kronberg et al., *Clinical Orthopaedics and Related Research*, No. 253, pp. 113-117, Apr. 1990.

Revision of Modular Humeral Components, Arroyo et al., *J. Shoulder Elbow Surg.*, vol. 8, No. 2, pp. 188-189, 1999 (abstract only).

rhead Radial Implant System, Avanta Orthopaedics, © 2000.

Robert et al., "The Geometry of the Humeral Head and the Design of Prosthesis," *The Journal of Bone and Joint Surgery*, vol. 73-B, No. 4, Jul. 1991.

Roidis, et al., "A Radiographic Study of Proximal Radius Anatomy with Implications in Radial Head Replacement," *Journal of Elbow Surgery*, vol. 12, No. 4, pp. 380-384, Jul./Aug. 2003.

Romeo, "Total Shoulder Arthroplasty: Pearls and Pitfalls in Surgical Technique," *Seminars in Arthroplasty*, vol. 6, No. 4, Oct. 1995.

Sequelae of Fractures of the Proximal Humerus: Surgical Classification and Limits of Shoulder Arthroplasty, Boileau et al., *Shoulder Arthroplasty*, pp. 349-358, 1999.

Shoulder Anatomy and Biomechanics, Flatow, *The Shoulder: Operative Technique*, pp. 1-42, 1998.

Shoulder Arthroplasty for Proximal Humeral Fractures: Problems and Solutions, Boileau, *Shoulder Arthroplasty*, pp. 297-314, 1999.

Shoulder Function After Displaced Fractures of the Proximal Humerus, Zyto et al., *J. Shoulder Elbow Surg.*, vol. 4, No. 5, pp. 331-336, Sep./Oct. 1995.

Soghikian et al., Complications of Humeral Head Replacement, *Complications of Shoulder Surgery*, pp. 81-92, © Feb. 1993.

Stress Analyses of Joint Arthroplasty in the Proximal Humerus, Orr et al., *Journal of Orthopaedic Research*, vol. 3, No. 3, pp. 360-371, 1983.

Surgical Treatment of Complex Fracture of the Proximal Humerus, Ko et al., *Clinical Orthopaedics and Related Research*, No. 327, pp. 225-237, 1996.

Survivorship of Unconstrained Total Shoulder Arthroplasty, Brenner et al., *The Journal of Bone and Joint Surgery*, vol. 71-A, No. 9, pp. 1289-1295, Oct. 1989.

The BiAngular Shoulder brochure, Biomet, Inc., © 1989.

The Complete Shoulder Solution brochure, Zimmer, Inc., © 1999.

The Effect of Articular Conformity and the Size of the Humeral Head Component on Laxity and Motion After Glenohumeral Arthroplasty, Harryman et al., *The Journal of Bone and Joint Surgery*, vol. 77-A, No. 4, pp. 555-563, Apr. 1995.

*The Elbow and It's Disorders 2$^{nd}$ Edition*, Morrey, Bernard F., pp. 16-20, 1993.

The Foundation Total Shoulder System brochure, Encore Orthopedics, 1996.

The Glenoid Components brochure, Wright Medical Technology, Inc., 1995.

The Intermedics Select Shoulder System, Intermedic Orthopedics, Inc., © 1992.

The Kirschner Integrated Shoulder System, Kirschner Medical Corp., © 1994.

The Krischner Integrated Shoulder System, Biomet, Inc. © 1994.

The Neer II Total Shoulder System, The 3M™ Modular Shoulder System brochure, Wright Medical Technology, Inc., © 1995.

The Normal Glenohumeral Relationships, Iannotti et al., *The Journal of Bone and Joint Surgery*, vol. 74-A, No. 4, pp. 491-500, Apr. 1992.

The Risk of Injury to the Axillary Nerve, Artery, and Vein from Proximal Locking Screws of Humeral Intramedullary Nails, Riemer et al., *Orthopedics*, vol. 13, No. 6, pp. 697-699, Jun. 1992.

The Roper-Day Total Shoulder Replacement, Roper et al., *The Journal of Bone and Joint Surgery*, vol. 72-B, No. 4, pp. 694-697, Jul. 1990.

The Shoulder Prosthesis in Four-Part Fractures: Problems and Solutions, Boileau et al., *Orthopedic*, vol. 4, No. 3, pp. 27-32, 1998.

The Three-Dimensional Geometry of the Proximal Humerus, Boileau et al., *The Journal of Bone and Joint Surgery*, vol. 79-B, No. 5, pp. 857-864, Sep. 1997.

Total Shoulder Arthroplasty: Revision for Instability, Moorman III et al., *Operative Techniques in Orthopaedics*, vol. 4, No. 4, pp. 237-242, Oct. 1994.

Total Shoulder Arthroplasty: Some Considerations Related to Glenoid Surface Contact, Ballmer et al., *J. Shoulder Elbow Surg.*, vol. 3, No. 5, pp. 299-306, Sep./Oct. 1994.

Total Shoulder Systems: Anatomy and Design, Pearl, Shoulder Arthroplasty: Arthroscopy and Arthroplasty, 16th Annual Meeting, pp. 44-49, Jun. 23, 1999.

Treatment of Humeral Shaft Fractures with Humeral Locked Nail and Comparison with Plate Fixation, Lin, *The Journal of Trauma Injury, Infection, and Critical Care*, vol. 44, No. 5, pp. 859-864, 1998.

*Treatment of Proximal Humerus Nonunions with the Polarus Humeral Rod: A Multicenter Study*, Davis et al., 1999 Annual Meeting Scientific Program, 1999.

Treatment of Three- and Four-Part Fractures of the Proximal Humerus with a Modified Cloverleaf Plate, Esser, *Journal Orthopaedic Trauma*, vol. 8, No. 1, pp. 15-22, 1994.

van Ri et, et al., "The Noncircular Shape of the Radial Head," *The Journal of Hand Surgery*, vol. 28A, No. 6, pp. 972-978, Nov. 2003.

Variations in the Retroversion of the Humeral Head, Edelson, *J. Shoulder Elbow Surg.*, vol. 8,.No. 2, pp. 142-144, Mar./Apr. 1999.

Vascularity of the Humeral Head After Proximal Humeral Fractures, Brooks et al., *The Journal of Bone and Joint Surgery*, vol. 75-B, No. 1, pp. 132-136, Jan. 1993.

Worsing, Jr., et al., "Reactive Synovitis from Particulate Silastic," *The Journal of Bone and Joint Surgery*, vol. 64-A, No. 4, pp. 581-585, Apr. 1982.

Yamashina, et al, "Open Reduction and Internal Fixation of Comminuted Fractures of the Radial Head Using Low-Profile Mini-Plates," *The Journal of Bone and Joint Surgery*, vol. 85-B, No. 7, pp. 1040-1044, Sep. 2003.

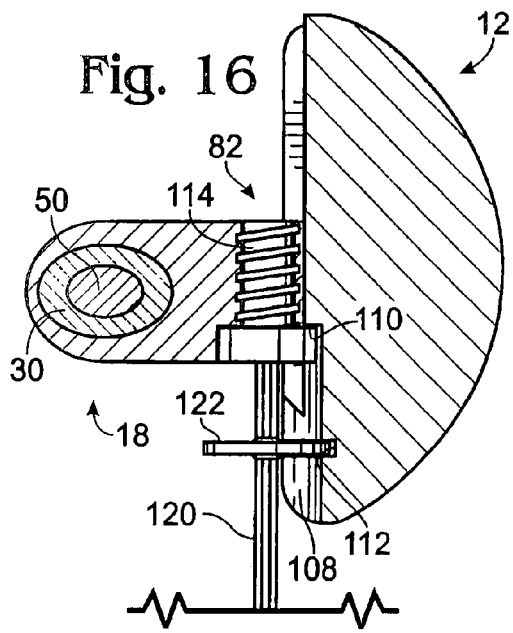
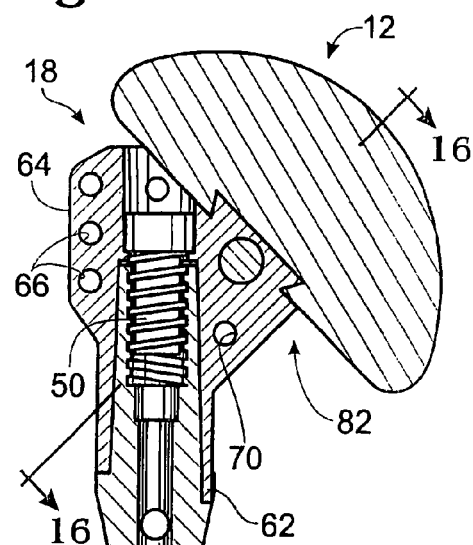
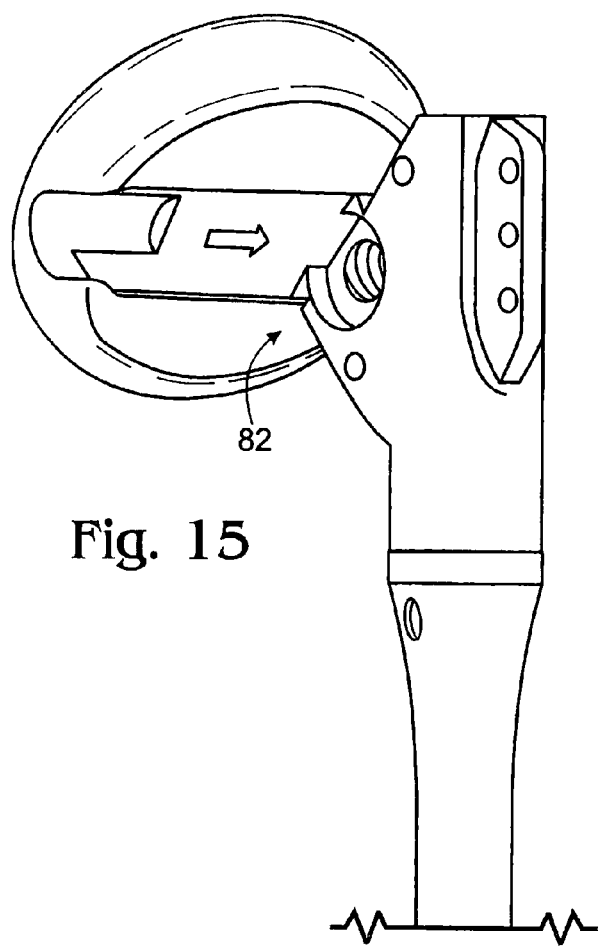

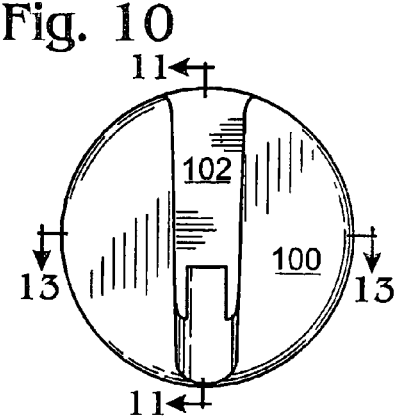
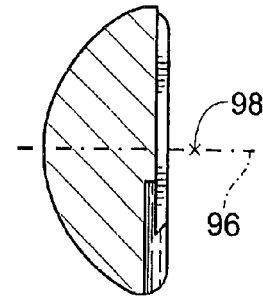
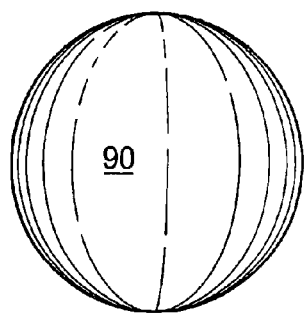
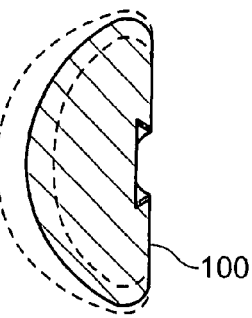
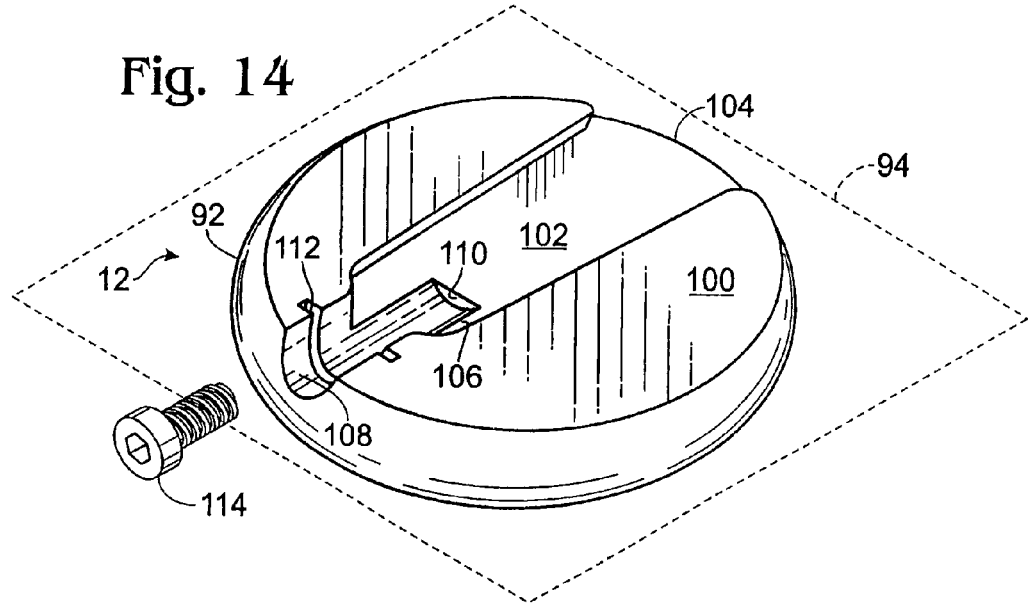

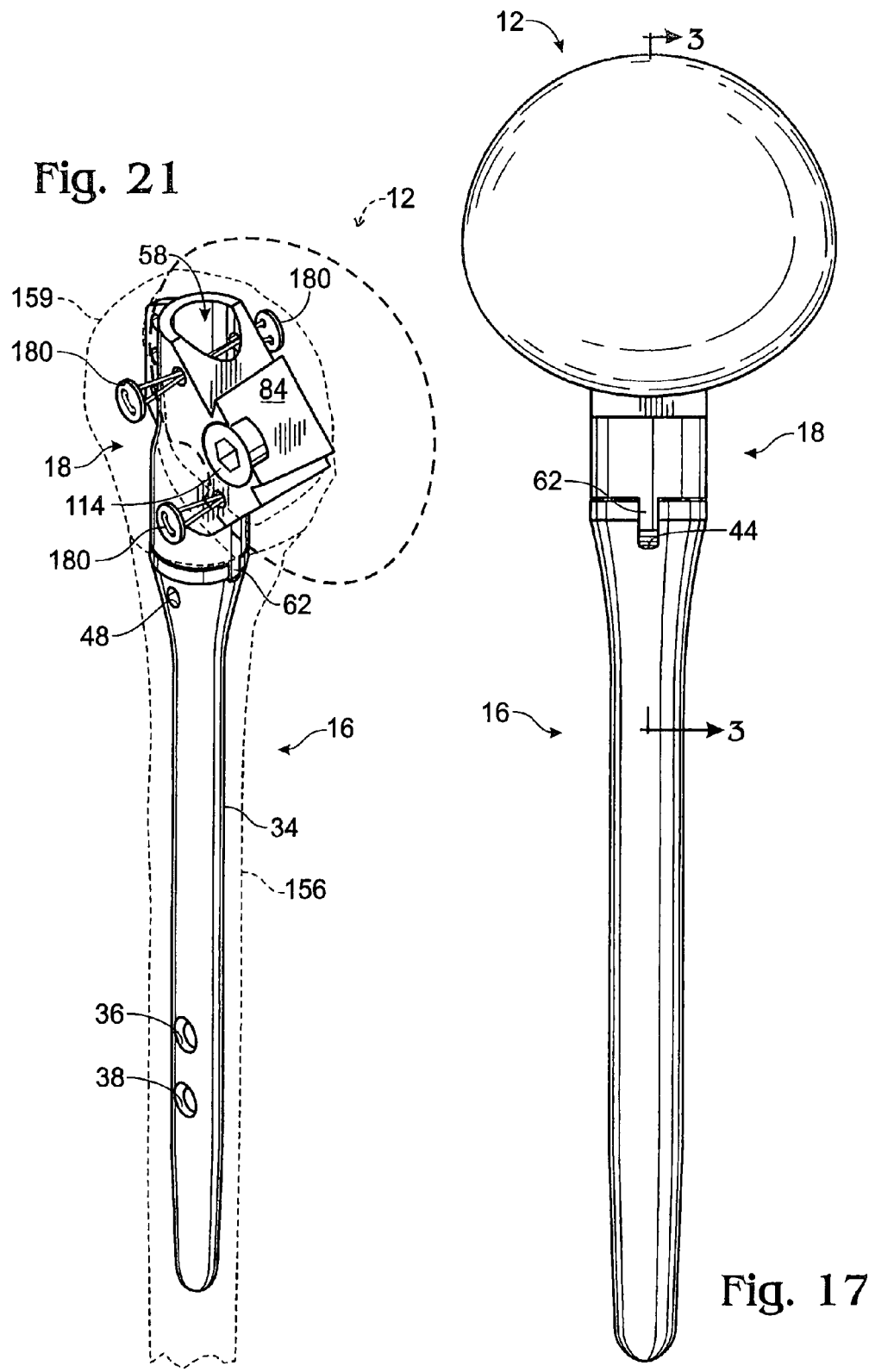

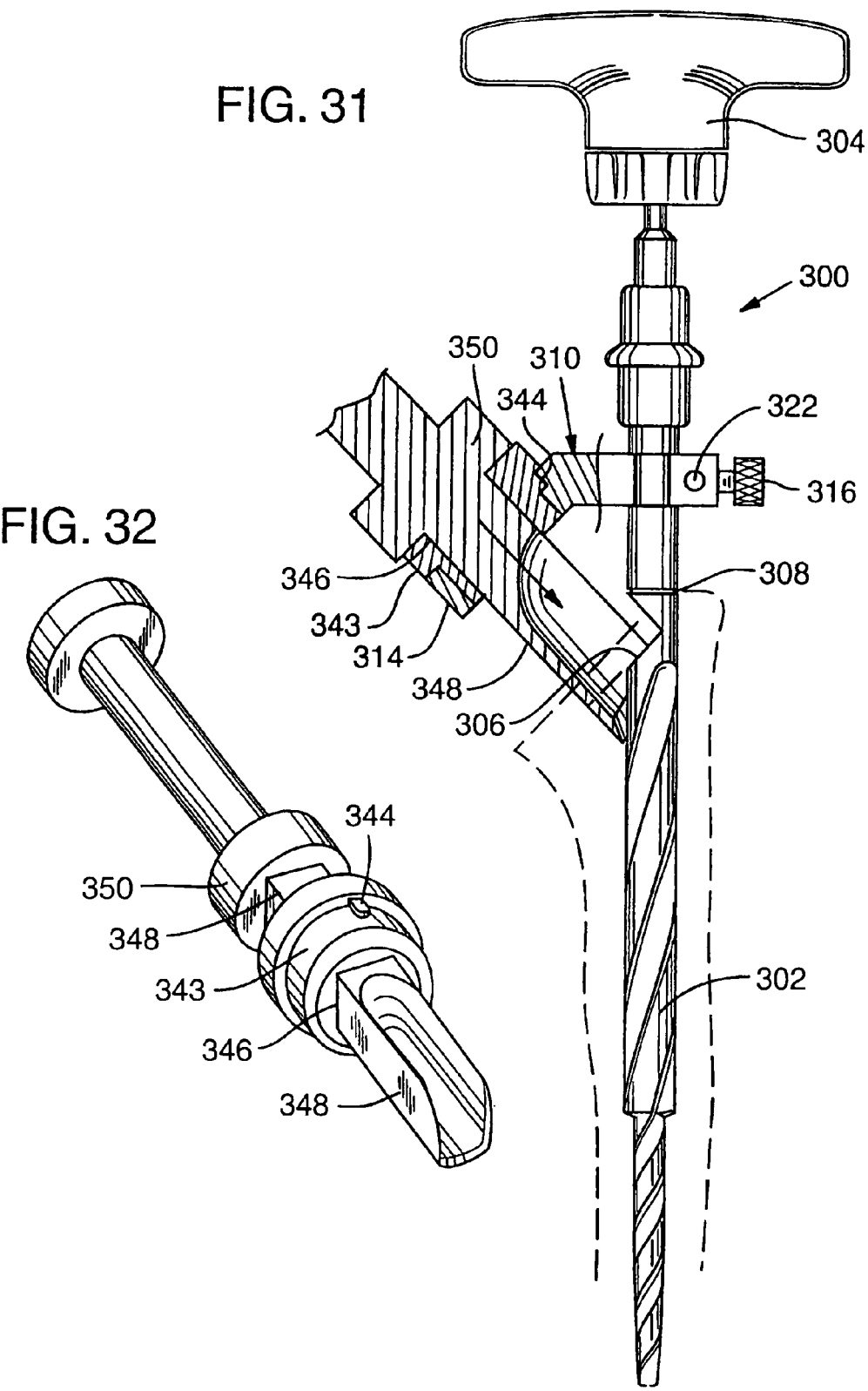

SHOULDER PROSTHESIS

CROSS-REFERENCE TO RELATED APPLICATIONS

This application is a continuation of U.S. patent application Ser. No. 10/321,282, filed Dec. 16, 2002, now U.S. Pat. No. 7,297,163, which, in turn, is a continuation of U.S. patent application Ser. No. 09/507,564, filed Feb. 18, 2000, now U.S. Pat. No. 6,494,913, which, in turn, is a continuation-in-part of U.S. patent application Ser. No. 09/191,928, filed Nov. 13, 1998, now U.S. Pat. No. 6,102,953, which, in turn, is a continuation-in-part of U.S. patent application Ser. No. 09/165,475, filed Oct. 2, 1998, now U.S. Pat. No. 6,193,758, and U.S. patent application Ser. No. 09/040,504, filed Mar. 17, 1998, now U.S. Pat. No. 5,961,555. These priority applications are each incorporated herein by reference in their entirety for all purposes.

FIELD OF THE INVENTION

This invention relates generally to bone prostheses and more particularly to a system for facilitating installation of a shoulder prosthesis.

BACKGROUND OF THE INVENTION

When a joint, such as the hip or shoulder, becomes impaired due to arthritis, disease or trauma, it is sometimes necessary to replace all or part of the joint with a prosthesis to restore function. For instance, hip replacement, where a prosthesis is provided to replace the femoral head and in some cases all or part of the acetabulum, has become a common procedure to treat femoral head fractures and arthritis in elderly patients. As a result of anatomical constraints and challenges in the shoulder, shoulder implants have historically been much less successful and less common than hip replacements. Recently, however, shoulder arthroplasty has emerged as an accepted treatment for severe arthritis and humeral head fractures.

As a consequence of the increasing acceptance of shoulder prostheses, many different devices have been developed to address various problems that have arisen and to offer additional benefits and features. In the simplest form, a shoulder prosthesis is formed as a single piece with a head to articulate with the glenoid cavity, and a stem to extend down the medullary canal of the humerus and support the head. While simple to construct, unitary implants do not offer any adjustability to accommodate the natural variations in size and geometry that occur among joints of different patients. To accommodate these variations, a large stock of devices must be manufactured and maintained to insure that an adequate match can be achieved during an operation. Stocking the large number of devices is a significant expense with one-piece designs, and in some cases a surgeon may not be provided with sufficient flexibility to achieve an ideal fit to the patient.

To avoid the expense of maintaining a large stock of single-piece prosthetics and to provide increased flexibility to surgeons, many shoulder implant makers have gone to a modular design that is assembled during the operation from two or three pieces. These pieces include a head to articulate with the glenoid and a stem structure on which the head is mounted and secured to the bone. In some cases, the stem includes a separate body portion disposed between the head and an intermedullary portion of the stem that extends down the medullary canal. By utilizing a modular design, a wide variety of devices can be assembled from only a few pieces, thus providing increased flexibility to accommodate anatomical variation and eliminating much of the cost associated with maintaining a large selection of one-piece devices.

Existing modular shoulder designs most commonly rely on a taper lock mechanism to secure the head to the rest of the implant. In at least some devices the portion of the taper lock on the head is offset to compensate for anatomical posterior offset of the humeral head. For instance, the taper lock portion on the head may be offset by 2-4 millimeters. By rotating the head, any offset between plus and minus the 2-4 millimeters can be achieved. Unfortunately, rotating an offset head can introduce a medial/lateral and/or superior/inferior offset at the same time the anterior/posterior positioning is adjusted. Furthermore, the offset between the center of the taper lock and the geometrical center of the head creates a torque which tends to rotate the head relative to the remainder of the implant, thereby increasing the chance of loosening of the head. As the offset increases, the resultant torque increases as well, making this a greater problem for larger offsets. Although such problems are incumbent in existing offset head designs, a posterior offset is generally desirable to better match the natural anatomy.

In addition to the specific drawbacks associated with various existing implant designs, there are a number of general problems inherent in shoulder replacements. In particular, it is generally difficult to establish the proper position and orientation for the implant in the humerus. One of the more important variables is the rotational position, or retroversion, of the head on the humerus. Anatomically, the average retroversion between a plane defined by the perimeter of the anatomical head and the axis of the flexed forearm is approximately 30-degrees. Unfortunately, with existing implants and techniques for their installation, it has been very difficult to reliably reproduce desired retroversion. Establishing correct retroversion is important because incorrect retroversion can lead to problems with subsequent dislocation.

In addition to the retroversion of the implant, it is necessary to establish the correct height of the implant on the humeral shaft. With existing designs, the surgeon slips the stem into the medullary canal and makes an educated guess at the proper height. Excess height may create too much tension in the deltoid, while inserting the implant too far down the humerus can result in deltoid lag. Similarly, the offset of the face of the head relative to the stem must be established correctly or excess or insufficient tension in the rotator cuff may be created. Unfortunately, with existing designs there is no way to evaluate implant height or head offset prior to final installation, after which correction is difficult.

When an implant is used as treatment for an arthritic shoulder joint, it is necessary to remove the existing humeral head and prepare the proximal end of the humeral shaft to receive the implant. It is important that the humeral preparation be accurate so that the position of the implant, which is determined in part by the configuration of the proximal end of the humerus, replicates the original anatomic position of the humeral head.

SUMMARY OF THE INVENTION

The present invention is a system and method for installing a shoulder prosthesis having a head and an elongate stem portion including a proximal end connected to the head, a distal section for insertion into a medullary canal of a humeral bone. The method includes removing the original humeral head and shaping the proximal end of the humerus with one or more implements to prepare the humerus to receive the shoulder prosthesis.

BRIEF DESCRIPTION OF THE FIGURES

FIG. 3 is a cross-sectional view of a shaft of the implant of FIG. 1.

FIGS. 10-13 are various views of a head portion of the implant of FIG. 1.

FIG. 14 is an isometric view of the backside of the head of FIGS. 10-13.

FIG. 15 is an isometric view of the head partially installed on the body.

FIG. 16 is a cross-sectional view of the implant along line 8-8 of FIG. 3.

FIG. 17 is a medial elevational view of the implant of FIG. 1.

FIG. 21 is an isometric view of the implant of FIG. 1 in an assembled configuration.

FIG. 31 is a side elevational view of the reamer of FIG. 26 and showing a chisel cutting instrument and a chisel bushing installed in the cutting guide. The chisel cutting instrument, chisel bushing, and a portion of the cutting guide are shown in cross-section.

FIG. 32 is an isometric view of the chisel cutting instrument and chisel bushing of FIG. 31.

DETAILED DESCRIPTION

Figure 1:
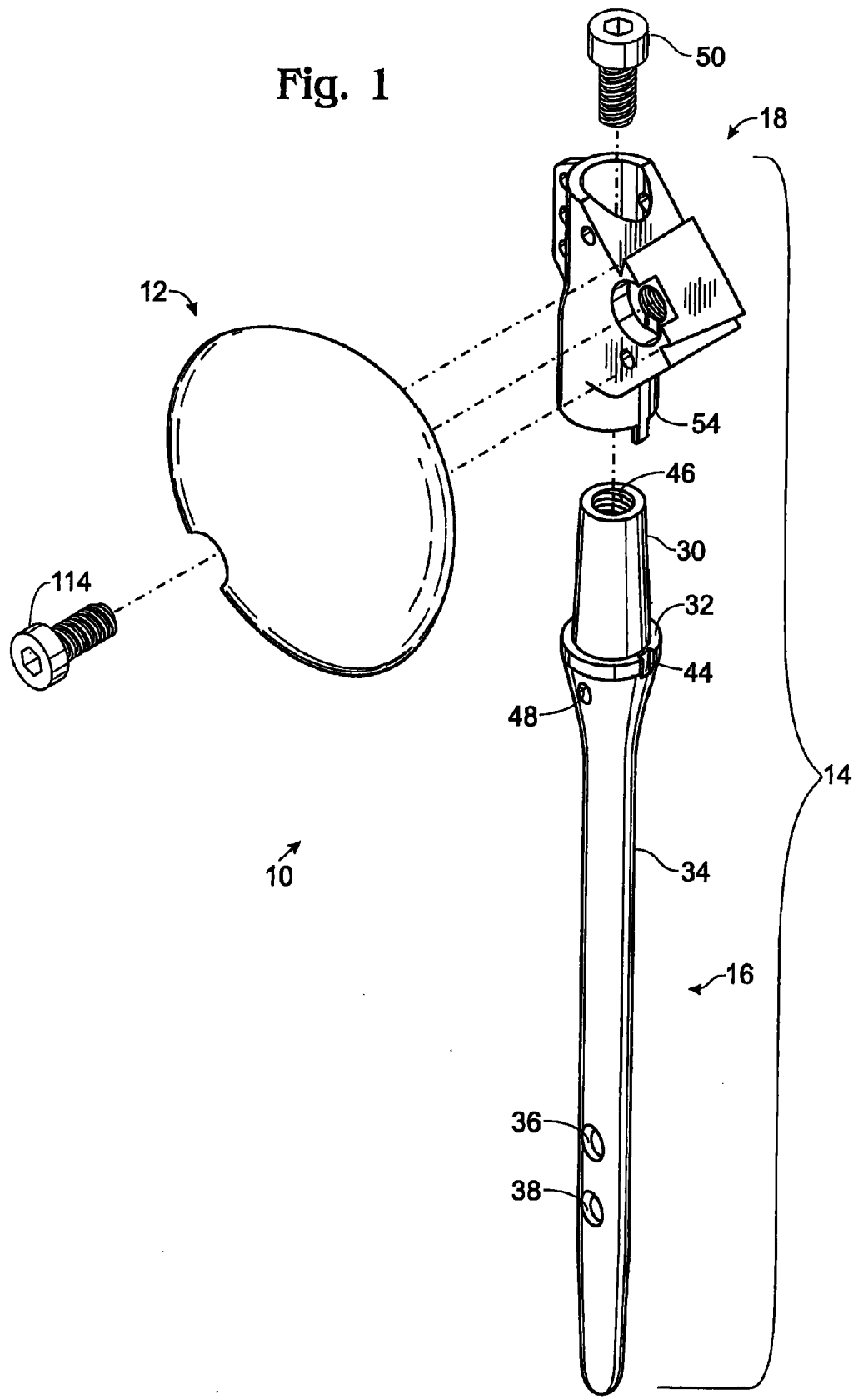
FIG. 1 is an exploded isometric view of a modular shoulder implant constructed according to the present invention.
Figure 2:
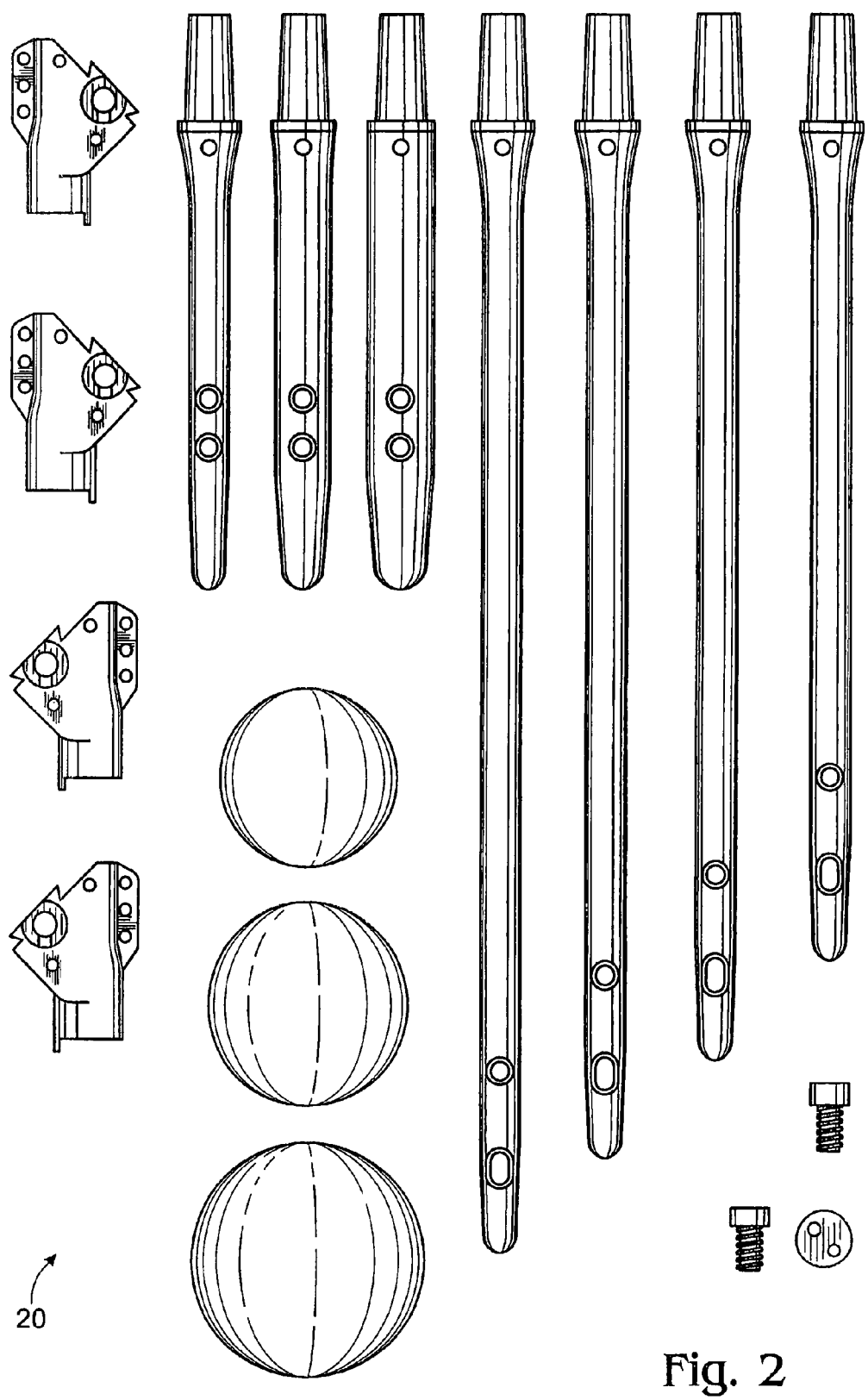
FIG. 2 shows a modular shoulder implant kit constructed according to the present invention.
Figure 4:
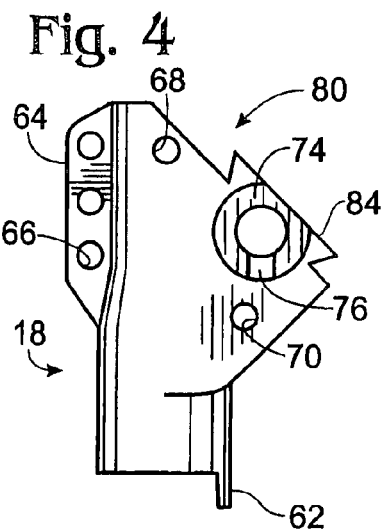
FIGS. 4-9 are various views of a body portion of the implant of FIG. 1.
Figure 5:
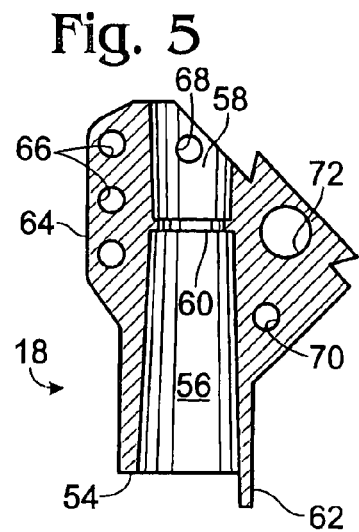

A shoulder implant constructed according to the present invention is shown generally at 10 in FIG. 1. Implant 10 includes a head 12 and a stem 14. The stem preferably includes a distal shaft 16 and a body 18. The components making up implant 10 are preferably chosen from a kit 20 of interchangeable shafts, bodies and heads, as shown in FIG. 2. By selecting an appropriate shaft, body and head from kit 20, a surgeon is able to create an implant that is sized properly for almost any patient. Positional references such as anterior/posterior, medial/lateral and proximal/distal used herein are made with reference to an implant as it would be positioned in a patient.

Shaft 16 is shown in greater detail in FIG. 3 and includes a proximal tapered end 30 extending distally to a shoulder 32 which tapers smoothly into a cylindrical medial region 34 with distal locking holes 36, 38. As can be seen in FIG. 2, the shaft can have a medial region of varying diameter and/or varying length. Generally speaking, the longer shafts are used where there is a mid-shaft fracture in addition to the proximal trauma. The varying diameter short shafts are used to accommodate size variations in the proximal end of the humerus. Either or both of holes 36, 38 may be elongated to allow for movement of the medial region over the locking screws. This is normally desirable when the implant is used to treat a combined mid-shaft fracture.

A rounded and tapered distal tip 40 is formed on the end of medial region 34. Shaft 16 preferably includes a central canulation 42 which can be used to guide the implant into the humerus with the aid of a guide wire. As best shown in FIG. 1, an alignment notch 44 is formed in shoulder 32 to aid in establishing the correct orientation of the body on the shaft, as will be described below. A threaded hole 46 is formed in tapered end 30 to receive a screw 50 which is used to draw the body firmly onto the tapered end. A wiring hole 48 is provided just distal of shoulder 32 to allow tension band wiring to be secured through the implant. In addition, when the implant is to be cemented in place, a K-wire can be driven through humerus and hole 48 to fix the position of the implant while the cement cures.

As indicated in FIG. 1, body 18 mounts to the top of shaft 16. Referring to FIGS. 4-9, body 18 has a distal end 54 with a cylindrical tapering socket 56 extending upwardly therefrom into the body. Socket 56 is sized to receive tapered end 30 of shaft 16 and taper-lock thereto to allow the body to be securely mounted to the shaft. A proximal bore 58 extends from the socket to the top of the body to the previously discussed screw to engage the top of the shaft to draw it into the socket. A small rib 60 is provided in the bore to engage against the head of the screw.

A small finger 62 projects down from the distal end of body 18 adjacent the socket to engage alignment notch 44 as the body is installed on the shaft. See FIGS. 1 and 17. This ensures the proper rotational positioning of the body on the shaft so that the various holes in the shaft are oriented correctly. Body 18 further includes a lateral rib 64 with three suture holes 66 which aid in securing the fracture fragments to the implant. Upper and lower medial suture holes 68, 70 are also provided in body 18 to offer additional options in securing the fragments. A medially positioned, anteriorly oriented threaded hole 72 is formed in body 18 to receive a screw for securing the head to the body. Hole 72 also serves as a mounting point for a targeting/installation instrument used with the implant. A recess 74 is located at the top of the hole and includes a keying notch 76 for orienting the targeting/installation instrument. See FIGS. 1 and 4. The recess allows the screw head to install substantially flush with the surface of the body to minimize the amount of bone removal required to insert the stem into the humerus.

Figure 6:
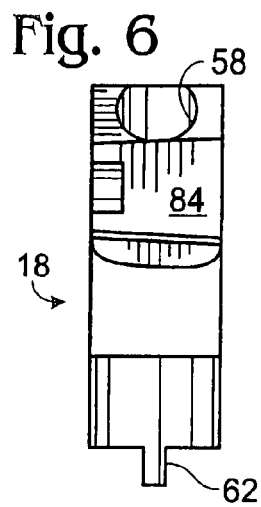
Figure 7:
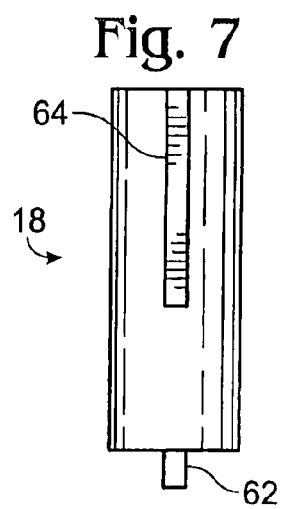
Figure 8:
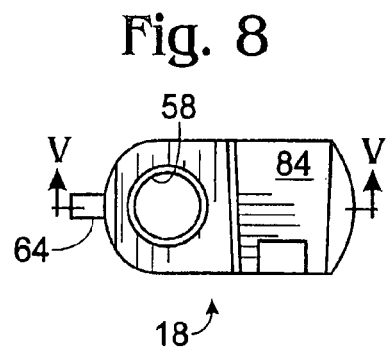
Figure 9:
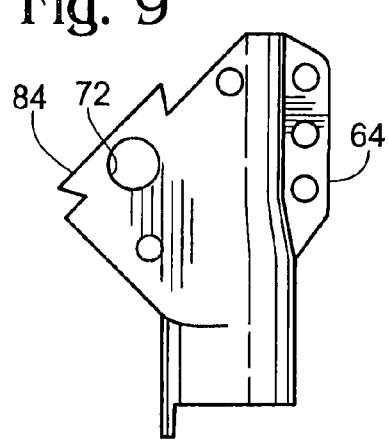

Body 18 includes a medially facing inclined mounting surface 80 at the proximal end onto which head 12 is mounted. Head 12 is secured to body 18 by coupling structure 82 which includes a fitting in the form of a pedestal or dovetail 84 located on mounting surface 80. As shown in FIGS. 6 and 8, dovetail 84 is tapered from anterior to posterior to establish a taperlock with the head, as will be described below. Because the dovetail is tapered, the body has a left or right orientation depending on which shoulder is to be replaced. Thus, as shown in FIG. 2, the kit will preferably include two or more bodies. Additional bodies, over and above one left and one right, may be provided to accommodate different stem diameters or head angles, etc.

Head 12, which is preferably formed as a unitary member, as opposed to being assembled from two or more components, includes a generally semi-spherical articulation surface 90 which is adapted to engage the glenoid cavity in the shoulder. See FIGS. 10-13. Because the glenoid cavity does not define a close fitting socket, such as found in the acetabulum in the hip joint, the articulation surface only needs to be sufficiently spherical to allow smooth articulation in the glenoid cavity.

As best shown in FIG. 14, articulation surface 90 is bounded by an articular margin 92 which defines an articular plane 94 generally normal to a head axis 96. In the preferred embodiment, where the head is substantially spherical, the head axis represents a central axis of rotational symmetry for the articulation surface and a center of curvature 98 lies on the head axis. See FIG. 11. As shown by the dotted lines in FIG. 13, the various heads are preferably formed with the same radius, but simply represent larger portions of a sphere. It is believed that this best reflects the actual anatomical characteristics.

In the most commonly occurring fracture pattern, the anatomic head fractures generally through the articular margin and plane. The articular plane defines generally the distal extent of head 12. This is important when it is necessary to remove the head as part of a revision procedure, because the present invention allows the head to be removed from an anterior direction without dislocation of the joint and the associated trauma. This is not the case with existing implant heads, which cannot be separated from the body for removal without first dislocating the joint. It is desirable, although not required, that the head not project substantially beyond the articular plane in the present invention so that it is possible to slide the head out of the joint in an anterior direction without disruption of the surrounding bone. Because the remainder of the humerus is distal to the articulation plane, the head may be slid out in that plane without disruption of the surrounding bone as long as the head does not project substantially beyond the articular plane. Thus, the coupling structure is adapted to allow the head to be installed on and removed from the stem without dislocating the shoulder after the implant has been installed in the shoulder.

Head 12 includes a mounting surface or backside 100 disposed opposite the articulation surface and separated from the articulation surface by the articular margin. Backside 100 includes a portion of coupling structure 82 in the form of a transverse track or undercut channel 102. Channel 102 is cut to match the cross-sectional shape and taper of dovetail 84 and includes an open end 104 and an inner end 106. A cylindrical recess 108 extends from the perimeter of the head past the inner end of the channel and to a stop 110. A groove 112 is formed in recess 108 near the edge of the head.

The channel is sized so that the head is guided onto the body and the dovetail taperlocks in the channel when the head is properly positioned. See FIG. 10. The taperlock connection is important because it rigidly secures the components and prevents them from fretting against each other and generating debris over time. The coupling structure of the present invention may also be described as a transversely acting taper lock, with a portion of the taper lock being disposed on the head and a portion disposed on the body. The taper lock of the present invention is transverse acting in that it does not rely on motion along the axis of the head to lock, contrary to existing designs. In fact, it can be seen that, when the head is engaged on the stem, the coupling structure mechanically interlocks the head against motion transverse to the articular plane. This is in contrast to existing designs, which simply rely on a frictional interconnection in the direction transverse to the articular plane.

A locking member in the form, of a screw 114 is provided to draw the head firmly onto the body to properly seat the taperlock. In particular, after head 12 is initially positioned on the body, as shown in FIG. 15, it is slid generally into position and screw 114 is installed into hole 72 with the head of the screw fitting closely into cylindrical recess 108. See FIG. 16. As the screw is driven in, the head of the screw engages stop 110 to pull head 12 firmly onto body 18. Screw 114 also serves as a backup interlock to insure that the head does not become dislodged. The head of the screw not seat completely against the body because some space must be left to accommodate machining tolerances in the coupling structure so that the taper lock may be drawn tight in all cases.

When it is necessary to remove the head, as in a revision, a tool 120 with a flange 122 secured near the tip of the tool is utilized. See FIG. 16. The tip of the tool is initially installed in the screw head from a slight angle away from the head and then the tool is rotated toward the head to engage the flange with taper breaking surface in the form of a groove 112 formed in recess 108. As the screw is backed out, the flange pulls against the head to dislodge the taperlock. Thus, the head can be removed with application of external force to the implant, as has been required with prior designs. This reduces the chance that the entire implant will be loosened when only the head needs to be removed.

Figure 18:
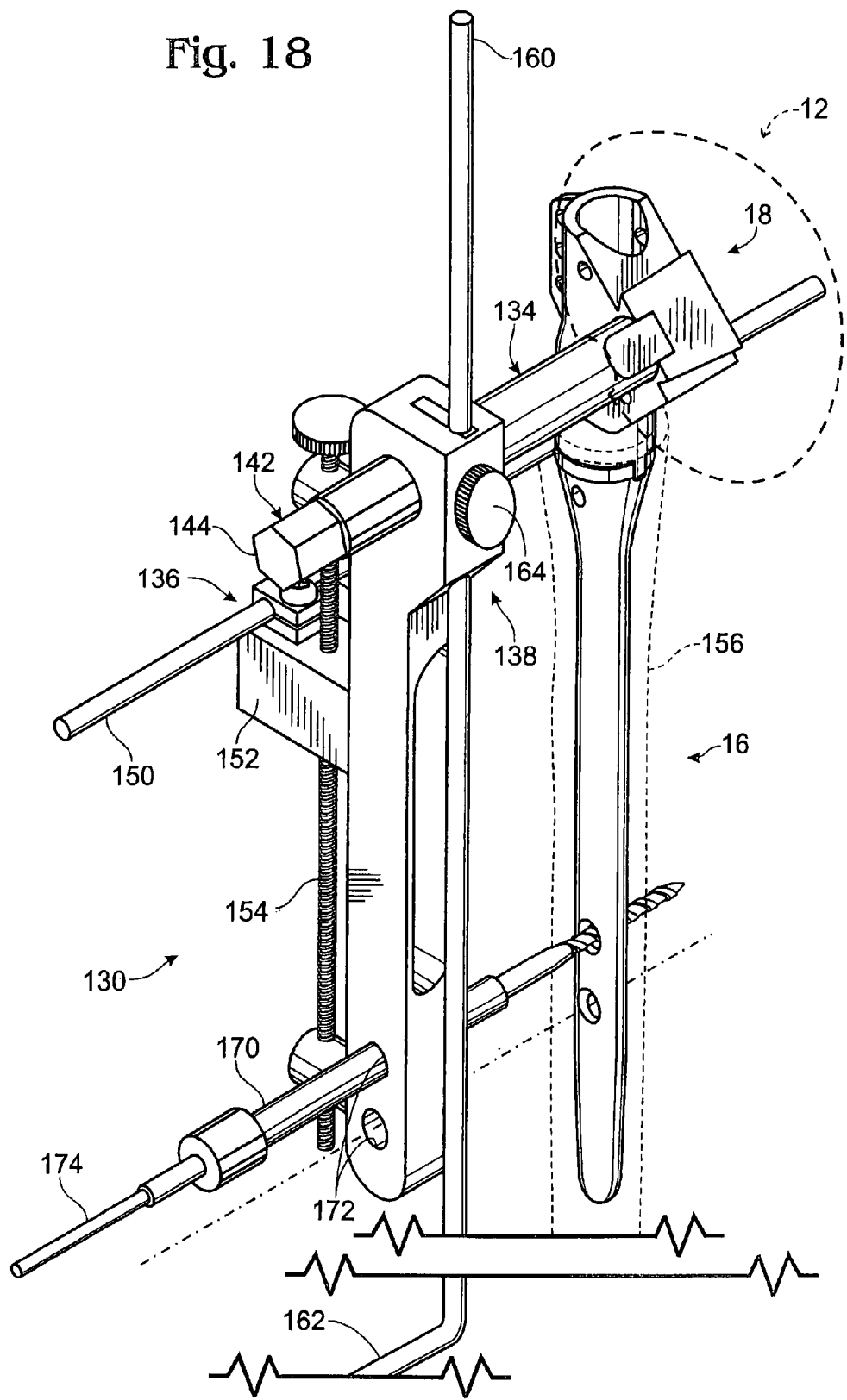
FIG. 18 is an isometric view of a targeting/installation instrument according to the present invention.

Installation of the implant of the present invention is facilitated by a targeting/installation instrument, shown generally at 130 in FIG. 18. Instrument 130 includes a template member 132 to which are mounted a mounting bar 134, a height adjusting mechanism 136 and a retroversion guide 138. Mounting bar 134 serves to join template member 132 to implant 10. In particular, bar 134 is hollow and includes a tab 140 (not shown) at the free end. The bar receives a bolt 142 with a head 144 and a threaded end 146. To attach the instrument to the implant, the free end of the bar is placed in recess 74 and aligned so that tab 140 fits into keying notch 76. This establishes the correct alignment between the template and the implant. The threaded end of the bolt is then screwed into hole 72 to secure the instrument to the implant. The bar includes a flat 148 to allow the bar to reach body 18 without engaging head 12. In addition, the screw that secures the head to the body is not installed until after the instrument is removed.

Once the instrument is mounted to the implant, the stem is inserted into the shaft of the humerus. In the typical fracture pattern, the head and greater and lesser tubercles are separated from the remainder of the humerus, leaving a pipe-like upper shaft. As a result, there is no remaining reference for the correct height of the implant head relative to the top of the humeral shaft. It is important to position the head at the correct height relative to the humeral shaft to avoid excess tension on the deltoid muscle by having the head too high or deltoid lag where the head is too low and the deltoid must undergo some contraction prior to starting to move the arm.

Figure 19:
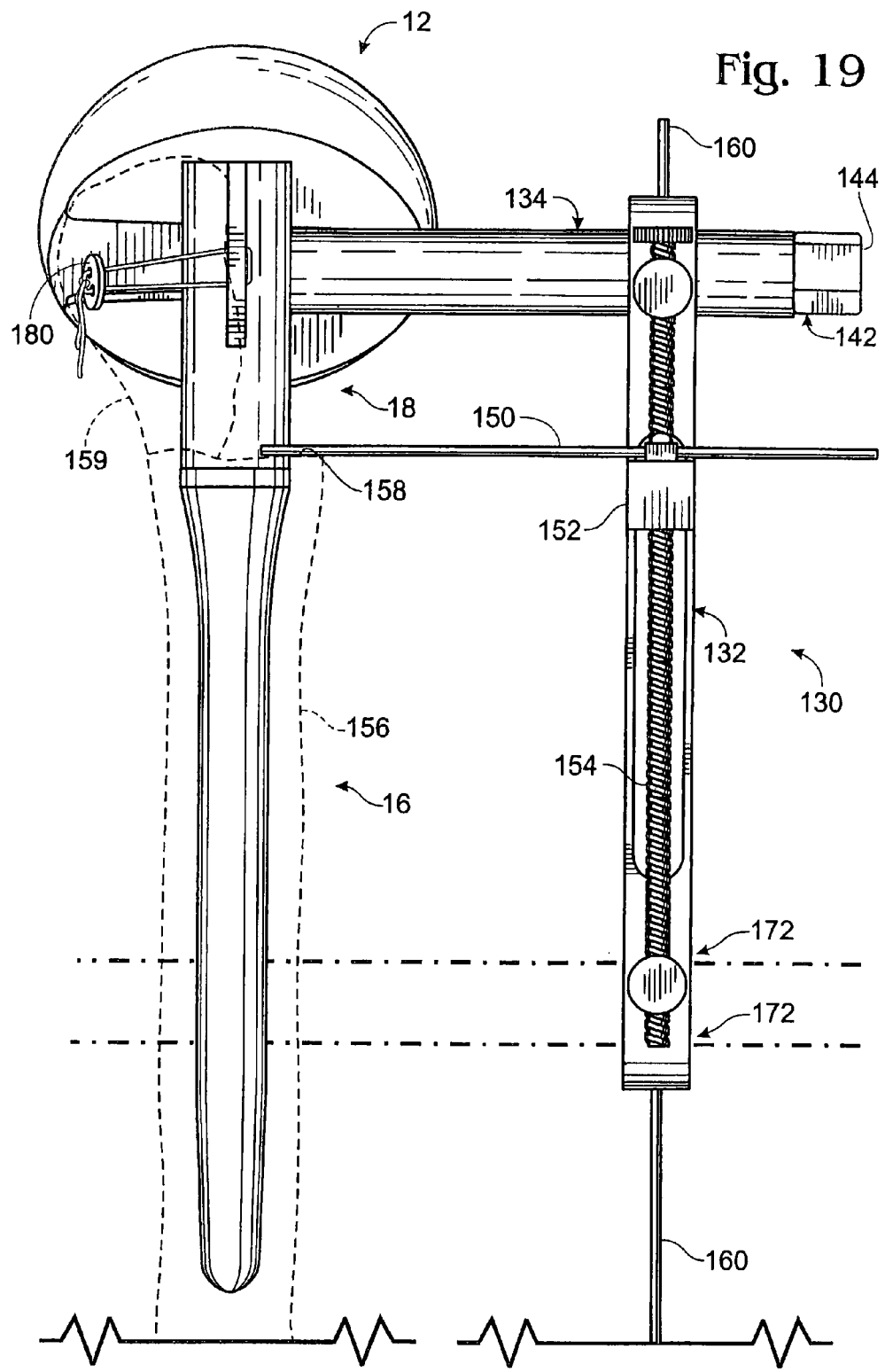
FIG. 19 is a lateral elevational view of the targeting/installation instrument of FIG. 18.

The height adjusting mechanism allows the surgeon to temporarily set the height of the head and then evaluate the deltoid tension. In particular, as shown in FIGS. 18 and 19, height adjusting mechanism 136 includes a guide bar 150 which is moveably mounted to a carriage 152, which is driven up and down along a threaded rod 154. With the implant in a humeral shaft 156, the guide bar is positioned to sit on top 158 of the humeral shaft. The surgeon can then adjust the implant up or down by turning the threaded rod. The guide bar establishes a predetermined height, which can be maintained while retroversion is set and even if the implant is removed and reinserted, as when bone cement is used.

Figure 20:
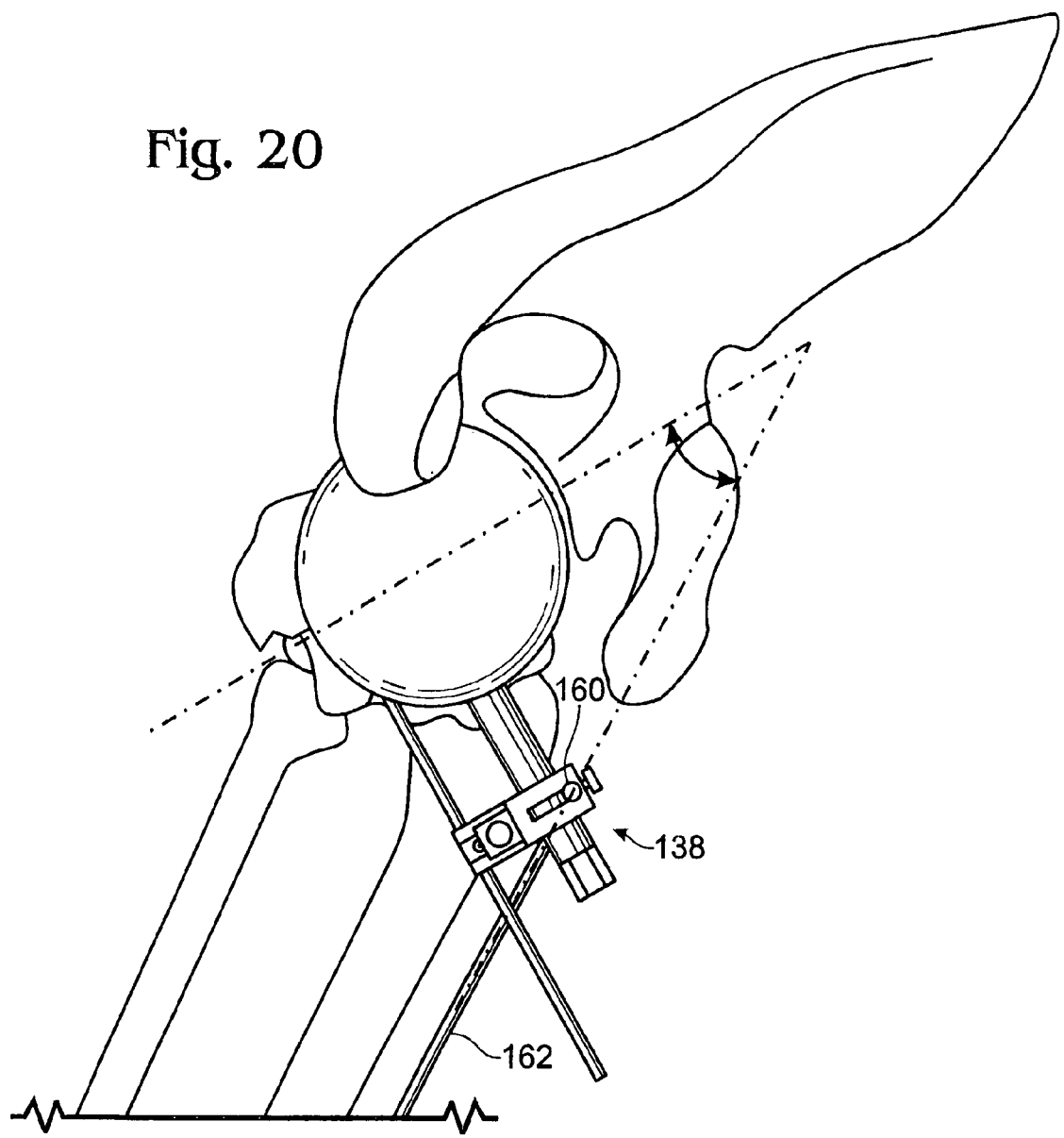
FIG. 20 is an elevational view from above of the targeting installation instrument of FIG. 18.

After establishing the correct height the surgeon can use the retroversion guide to set correct retroversion, as shown in FIG. 20. The retroversion guide includes an L-shaped rod 160 with a lower sighting arm 162. Rod 160 is pivotally and slidably mounted to template 132 to allow the height and angular orientation of the sighting arm to be adjusted. A set screw 164 allows the position of the rod to be fixed once it is in the desired orientation. In use, the sighting arm is set for a predetermined retroversion angle relative to the head axis, for instance 30-degrees. This can be accomplished before attachment to the implant using a protractor jig (not shown). With the sighting arm set to the correct orientation, the patient's forearm is flexed to approximately 90-degrees to the humerus. The surgeon then rotates the implant to align the sight arm with the axis of the forearm, thereby easily and accurately establishing the desired retroversion.

Once the correct height and retroversion is established, a cannulated drill guide 170 is inserted through guide holes 172 provided in the distal end of the template member. See FIG. 18. Guide holes 172 are oriented to target locking holes 36 in the end of the stem. A drill 174 is inserted though the drill guide to bore through the bone over the locking holes. One or two screws are installed through the humerus and locking holes to secure the implant in place.

As shown by the dotted lines in FIG. 19, it is possible to attach the greater tubercle 159 to the implant prior to final securing of the head. This allows the surgeon to evaluate the tension in the rotator cuff and make corrections, if necessary, by moving to a smaller or larger head. One other feature of the present invention is the provision of suture supports 180, shown in FIG. 21, which serve to distribute the force of the suture over the bone. Particularly in trauma cases, the bone is very soft and without supports 180, the sutures will sometimes pull through the bone. By utilizing the supports, the surgeon can obtain the desired suture tension without risk of the suture pulling through the surface of the bone.

The targeting/installation instrument is provided in left and right versions, although it would also be possible to make mounting bar 134 reversible or symmetric to accommodate left and right bodies. In addition, a longer template member would be used with the longer shafts used to treat mid-shaft fractures.

Figure 22:
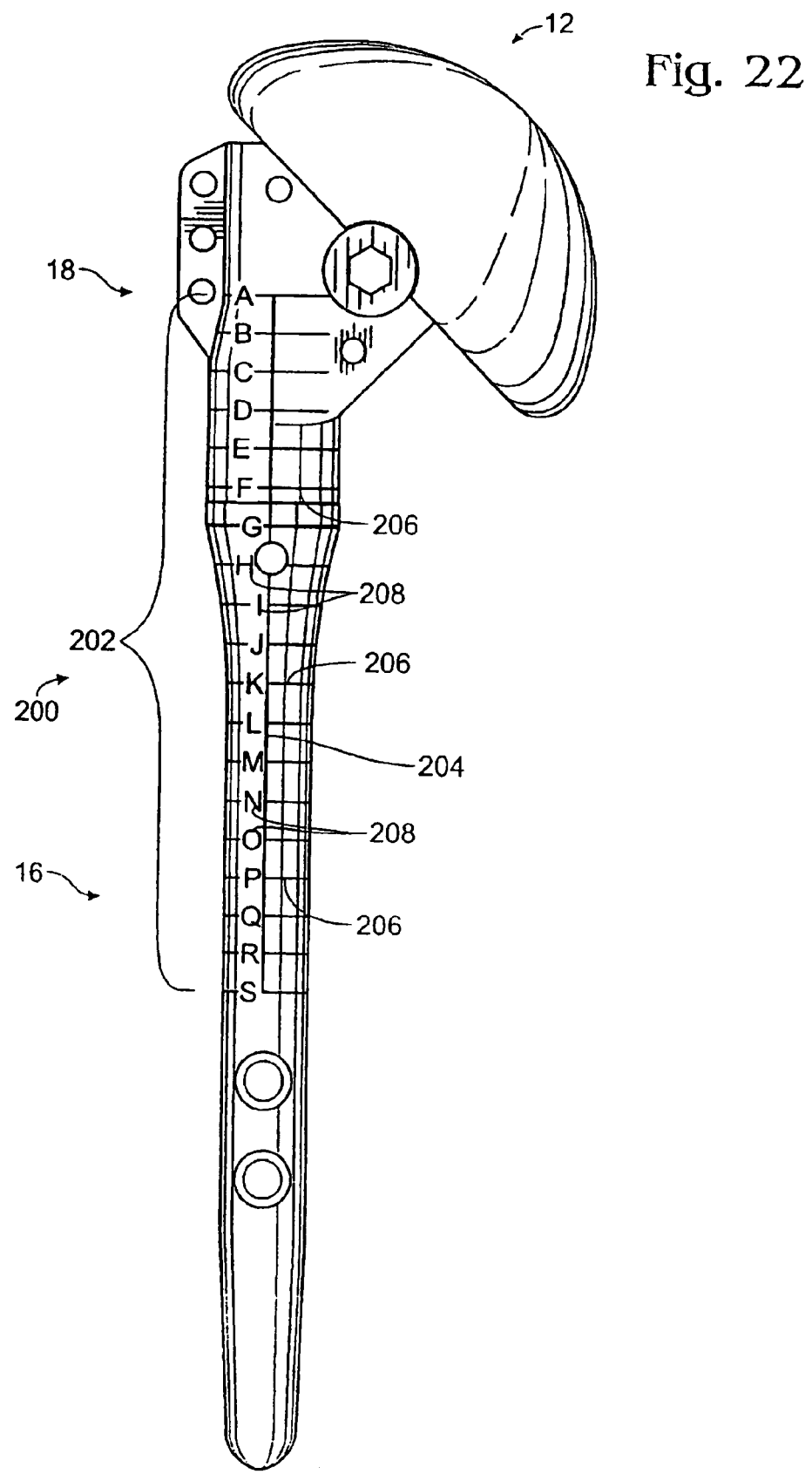
FIG. 22 is a side elevational view of an implant showing reference marks.

Installation and alignment of the implant can also be facilitated by placing indications or reference marks on the implant, as shown at 200 in FIG. 22. Reference marks 200 are placed in an alignment section 202 of the stem, generally in the area of the stem, which will lie adjacent the top of the humeral shaft when installed. Preferably, the reference marks include one or more angular marks such as angular indication 204 and multiple vertically spaced gradations 206, allowing both height and angular orientation to be monitored. A plurality of indicia such as letters 208 are applied to the vertically spaced gradations marks at intervals to make identifying a particular gradation easier. The marks can be laser marked on the surface of the implant, etched into the implant or applied via any other standard marking process. The marks and indicia would normally be viewed from the anterior direction and are therefore preferably placed on that side. In the case of implants that can be placed on either the left or right side, the marks and indicia would preferably be formed on both sides of the implant so that they were visible in either case.

In use, the surgeon first installs one or more trial prostheses to obtain proper fit and positioning in the fashion described above. The trial prostheses are typically identical to the actual prosthesis, but are assembled from a kit of components that are reused from operation to operation. The trial prostheses are equipped with reference marks at the same locations as the actual prosthesis. Once the correct fit and positioning are established, the surgeon notes which gradation is positioned adjacent to the top of the humeral shaft. The surgeon then marks the bone with a methylene blue dye marker at the top of the shaft in line with the angular indication. The surgeon can then take the actual implant and place it in the bone and replicate the trial position, which includes an angular orientation and a depth component, by aligning the previously noted marks on the actual implant with the previously determined location on the bone.

The alignment marks may be implemented on a modular or unitary implant and may be used alone or in conjunction with the above-described targeting instrument. Moreover, such marks are beneficial, even when used without a trial device, to verify that an implant has not moved after the desired position has been established.

Figure 23:
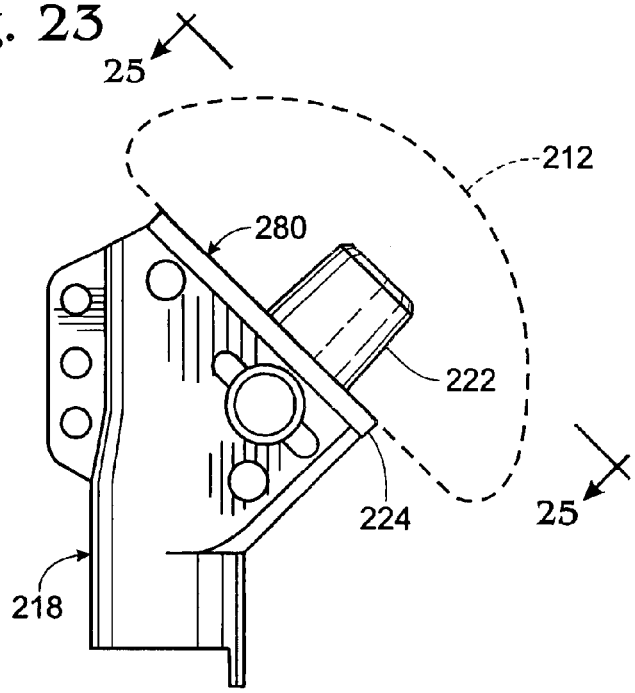
FIG. 23 is a side elevational view of a body constructed according to the present invention.

Another embodiment of a body for use with a shoulder implant according to the present invention is shown at 218 in FIG. 23. Body 218 is similar in construction to body 18, but includes a tapered stud 222 formed on an upper mounting surface 280. A head 212 is adapted to be mounted to body 218 by mounting on stud 222. More specifically, the head includes a tapered bore 226 which fits over stud 222 and is sized to form a taper lock therewith, thus securing the head to the body. See FIG. 24. A collar 224 forms the lower boundary of mounting surface 280. The collar serves to prevent the body from subsiding down into the humerus and creating an outward pressure on the head tending to loosen the taper lock.

Figure 25:
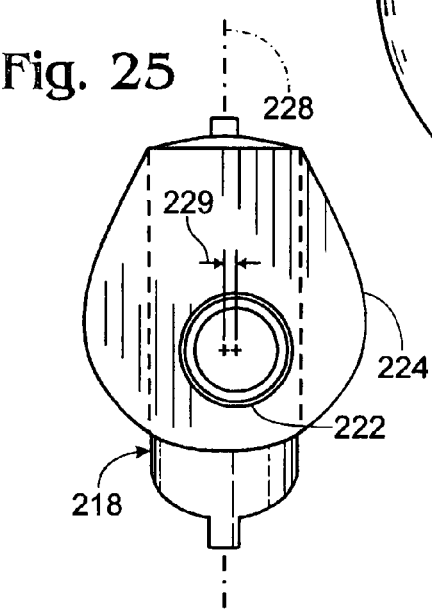
FIG. 25 is an elevational view along line 25-25 in FIG. 23.

As best seen in FIG. 25, the axis of the tapered stud is offset from an anterior/posterior plane 228 of the body and stem. In the disclosed embodiment, the offset, indicated at 229, is approximately two millimeters in the posterior direction, as implanted. Generally, suitable offset could be between approximately 1 and 5 millimeters. As a result of the offset, the bodies are provided in left and right versions, which are mirror images of each other.

Figure 24:
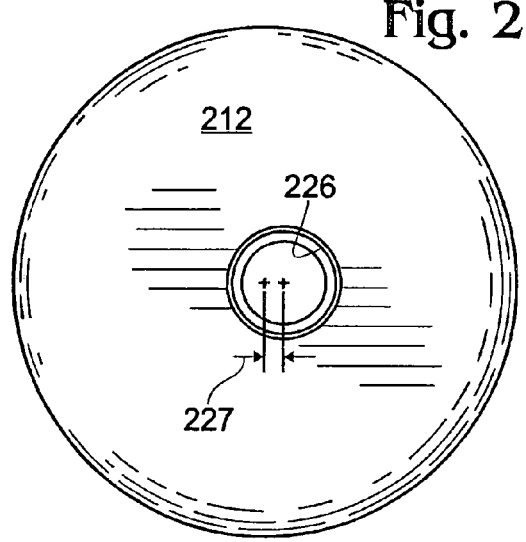
FIG. 24 is an elevational view of the rear surface of a head constructed according to the present invention.

In the disclosed embodiment, the tapered bore is positioned approximately 1 millimeter offset from the center of the head as depicted at 227 in FIG. 24. This offset allows the surgeon to rotate the head to achieve any desired offset between 1 and 3 millimeters. By offsetting the tapered stud from the anterior/posterior plane, the surgeon is able to achieve a range of posterior offsets without introducing excessive superior/inferior offsets. Although the head is shown with an offset, it is possible that the head might not have any offset, thus eliminating any superior/inferior offset. One of the benefits of eliminating head offset is that it is possible to introduce the desired anterior/posterior offset via the body without introducing other perturbations into the positioning of the head. It is generally desirable to keep the head offset to a minimum to reduce the torque created by the offset.

In addition to providing the body in left and right versions, it may be desirable to provide multiple left and right bodies with various offsets. Because heads are substantially more costly to produce than bodies, providing multiple bodies offers a more economical approach to achieving a wide variety of anatomical offsets. The body can be manufactured by machining from bar stock or may be cast. Another benefit of providing side-specific bodies is that the size of the body can be kept to a minimum in comparison to adjustable bodies. Minimizing the size of the body reduces the amount of bone that must be removed to install the implant.

The anterior/posterior offset described in the context of a cylindrical taper lock may also be implemented on the dovetail taper lock previously described by simply offsetting the taper lock in the head or on the body or both.

When one of the implants described above is used as treatment for arthritis rather than fracture repair, it is necessary to resect the humeral head. It is important that the resection process leaves a surface at the top of the humeral shaft with a correct retroversion, inclination and height because the resection-surface supports and orients the prosthesis. The first step in this process according to a preferred embodiment of the present system is to make a coarse resection of the head. The coarse resection can be accomplished with a saw, osteotome or other tool.

Figure 26:
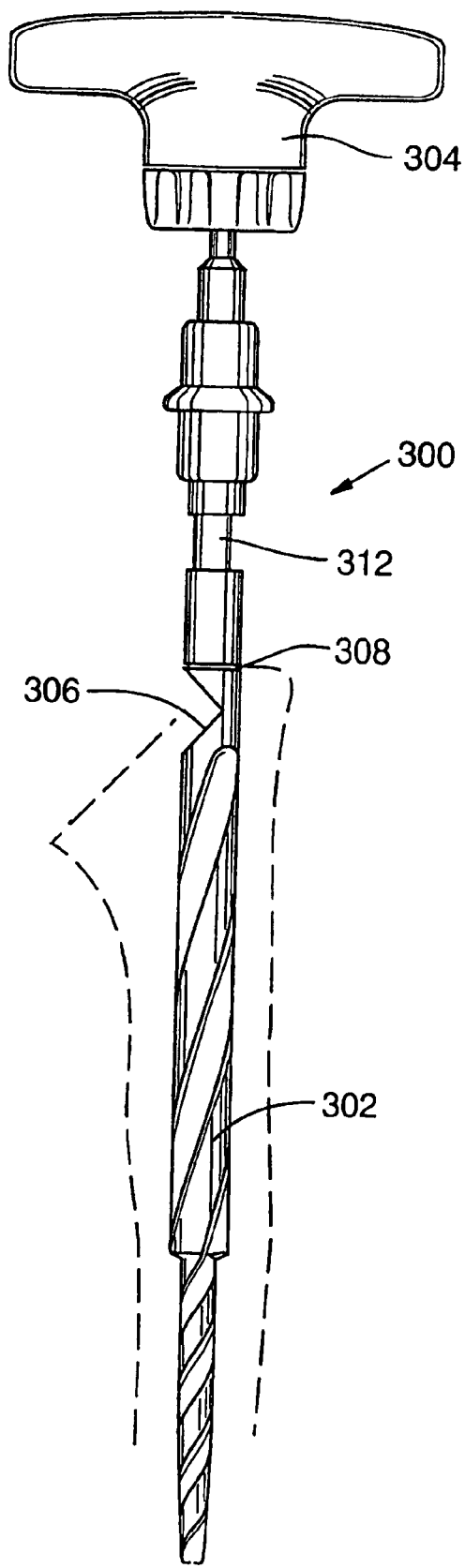
FIG. 26 is a side elevational view of a reamer disposed within the medullary canal.

Once the initial, coarse resection is complete, a reamer, such as shown at 300 in FIG. 26, is used to form a bore down the medullary canal of the humerus. Typically, one or more reamers of increasing size are used until the desired fit is obtained. The final size will depend on the size of the patient and the anatomy of the humerus. The final size should result in a relatively snug fit of the reamer in the medullary canal, which will translate to a correspondingly good fit of a distal portion of a stem with a size matching the reamer.

Reamer 300 includes a distal fluted section 302 and a proximal ratchet drive handle 304. A clearance notch 306 is located just below a depth line 308 or other suitable reference indicia. The reamer is driven in until the depth line is aligned with the top of the greater tuberosity. This depth is chosen to locate the head of the implant at the correct height in the subsequent steps. When the final reamer is driven so that the depth line is aligned with the top of the tuberosity, it is relatively stable and is used as a reference for the remaining steps. Use of a single reference structure for several or all of the preparation steps increases the accuracy and ease of preparing the humerus. It will be appreciated that while the resection method described herein includes using the reamer as a reference structure, it is within the scope of the invention to remove the reamer from the medullary canal after the bore is formed and install any suitable device as the reference structure.

Figure 27:
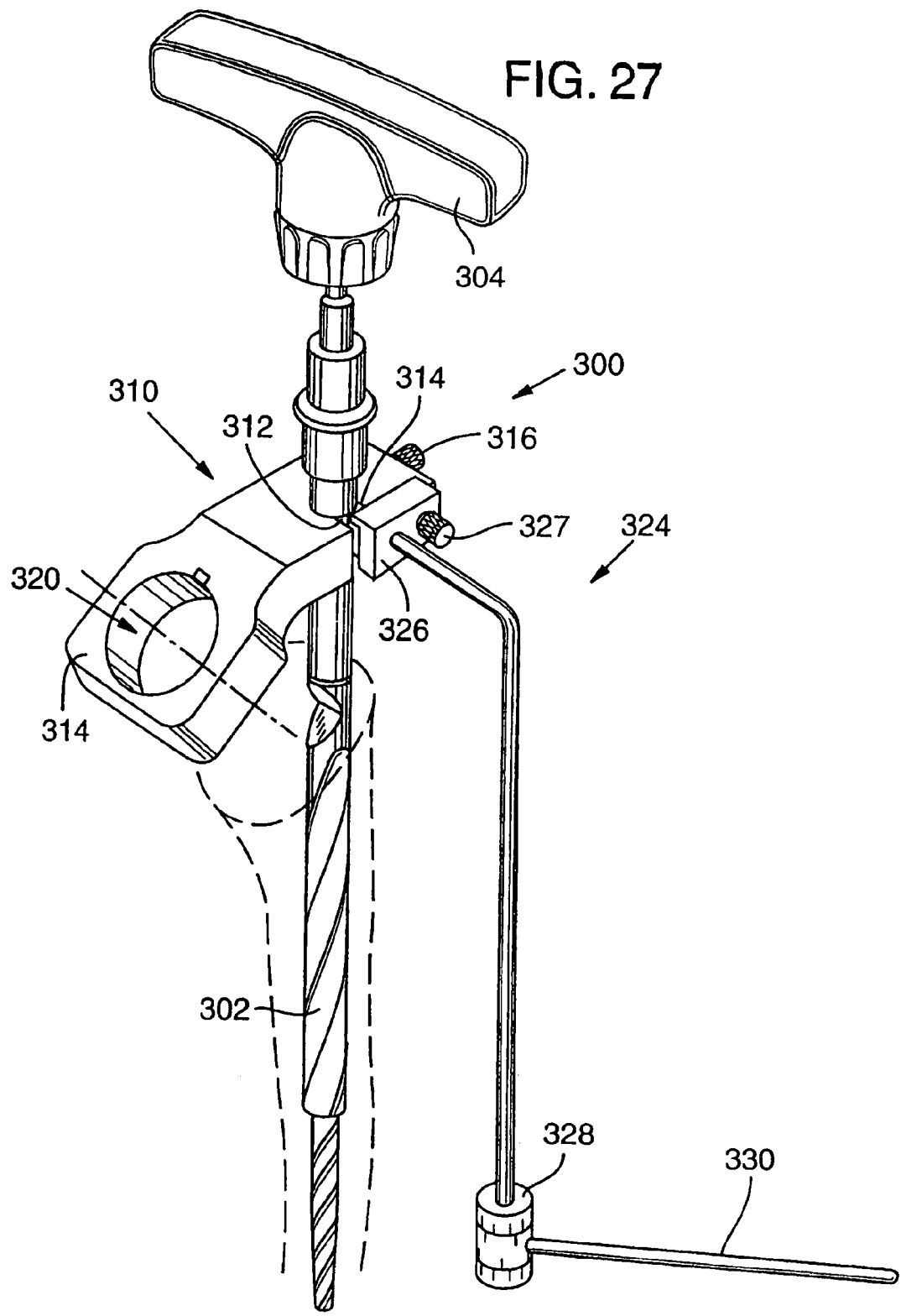
FIG. 27 is an isometric view of the reamer of FIG. 26 and showing a cutting guide attached to the reamer and an alignment structure attached to the cutting guide.

A cutting guide 310 is attached to reamer 300 at a neck 312. See FIG. 27. The cutting guide is the same thickness as the length of the neck and includes a notch 314 that fits over the neck. A screw 316 is tightened to secure the cutting guide on the reamer. The cutting guide includes a guide platform 318 with a central opening 320. The platform replicates the angle of the head of the implant. The central opening projects along a direction generally perpendicular to the desired resection-surface, down to the position of the head on the humerus.

Figure 29:
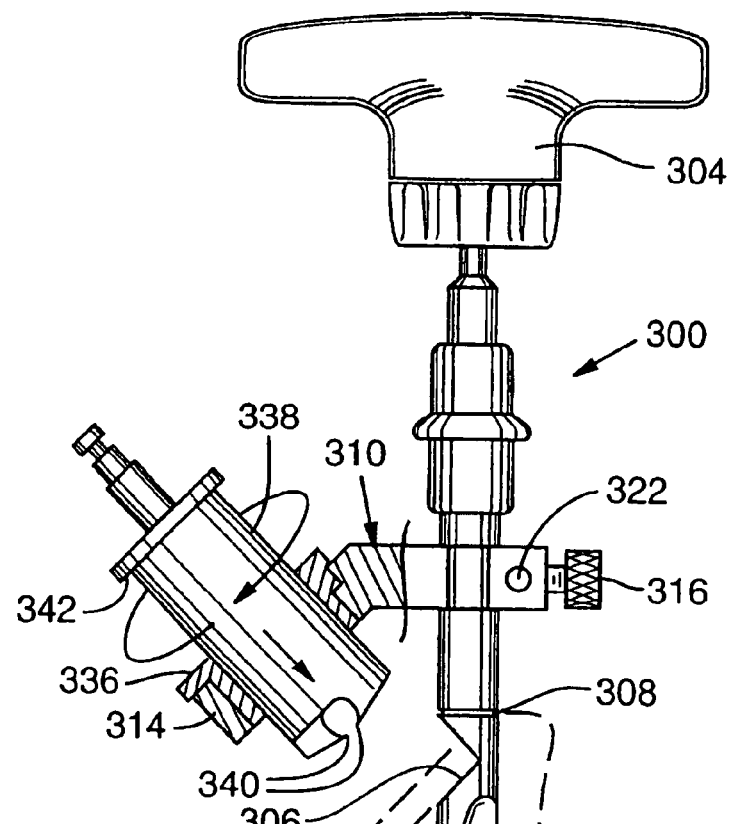
FIG. 29 is a side elevational view of the reamer of FIG. 26 and showing a counter-bore cutting instrument and a counter-bore bushing installed in the cutting guide.
Figure 30:
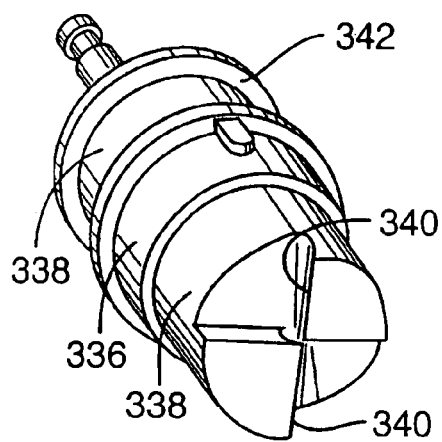
FIG. 30 is an isometric view of the counter-bore cutting instrument and counter-bore bushing of FIG. 29.

The cutting guide includes mounting holes 322 on each side (see FIGS. 29 and 31) for mounting a retroversion alignment structure 324. In particular, alignment structure 324 includes a bracket 326 disposed at one end with a screw 327 that fits into one of holes 322. The bracket holds the sighting arm with a predetermined orientation to the cutting guide. An indexed pivot coupling 328 connects a distal sighting arm 330 to the remainder of the cutting guide.

Figure 28:
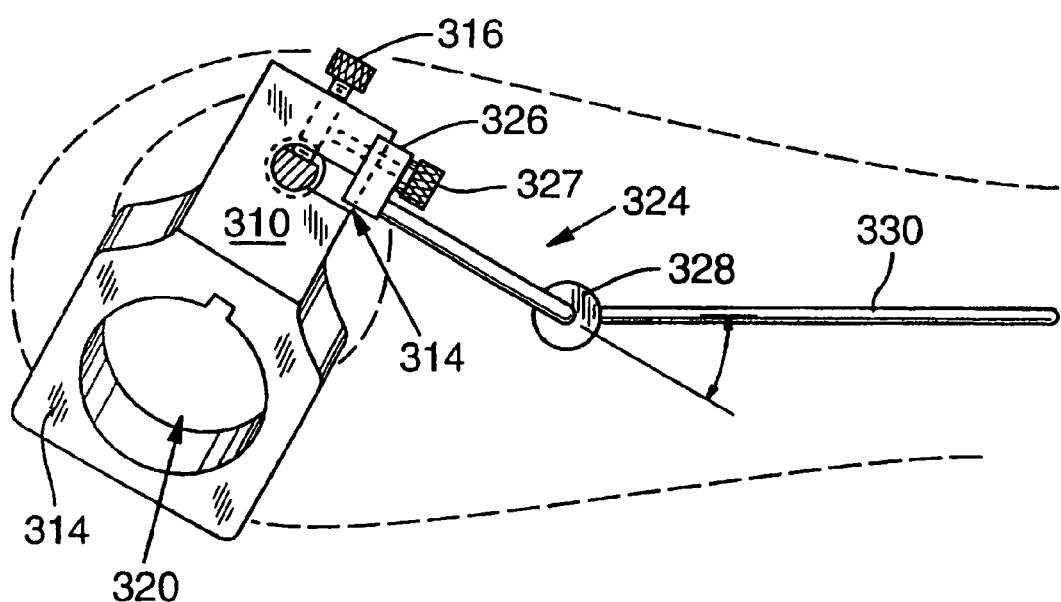
FIG. 28 is a top plan view of the reamer of FIG. 27, showing alignment of the alignment structure with the patient's forearm.

The indexed pivot coupling allows the sighting arm to be rotated incrementally, in intervals of ten degrees for instance. The pivot is marked so that the surgeon can select the desired retroversion angle indicated by the alignment structure, i.e., 30-degrees, and then rotate the cutting guide until the sighting arm is aligned with the forearm. See FIG. 28. As with the sighting arm used on the previously described positioning jig, the location of the sighting arm near the forearm rather that near the shoulder, although not required, allows the retroversion angle to be set more accurately and reliably. The reamer can be rotated with the cutting guide to achieve the correct retroversion.

Once the retroversion is set, the cutting guide defines the height, inclination angle and retroversion angle of the resection-surface by guiding one or more cutting instruments used to form the resection-surface. Since cutting guide 310 is attached to the reamer, the resection-surface is defined relative to the medullary canal, thus providing a customized fit to the humerus. Cutting guide 310 defines the resection-surface and guides the cutting instruments without requiring attachment to the humeral head. Thus, cutting guide 310 provides a simplified resection procedure over cutting guides which must be attached (e.g., by screws, etc.) to the humeral-head, and then removed after the head has been resected.

Exemplary cutting instruments are illustrated in FIGS. 29-32. Focusing first on FIGS. 29-30, a counter-bore bushing 336 is installed in the cutting guide. A counter-bore cutter 338 fits closely through the bushing and is aimed at the proper location on the humerus to counterbore a recess adapted to receive the prosthesis collar and/or the back side of the head. The cutter includes cutting edges 340 at the front end that remove bone in a flat circular area. The cutter is twisted to remove bone along a direction generally perpendicular to the resection-surface, until a shoulder 342 at the rear end of the cutter reaches the cutting guide. By this operation, a flat platform at the correct height, retroversion and inclination is created. Notch 306 allows the cutter to reach the full depth without striking the reamer. If necessary or desired, the bone material around the periphery of the recess platform may be removed or reduced by any suitable means.

Once the platform is properly shaped, a chisel bushing 343 is installed in the cutting guide, as shown in FIGS. 31-32. The chisel bushing has a key 344 to insure that bushing is installed in the guide in the correct orientation. The bushing includes a central opening 346 that is shaped to receive a hollow rectangular chisel 348. The bushing guides the chisel into the humerus at the proper location to form a recess adapted to receive the medial portion of the body. As with counter-bore cutter 338, cutting guide 310 guides chisel 348 along a direction generally perpendicular to the desired resection-surface. A shoulder 350 prevents the chisel from cutting too deeply into the bone. Once the recess for the implant body has been formed, the reamer and cutting guide may be removed from the humerus.

The result of the above steps is that humerus will fit very closely around the shoulder implant, without significant vertical, lateral or rotational play. This close fit leads to a more secure connection of the implant in the humerus and better surgical results.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. No single feature, function, element or property of the disclosed embodiments is essential to all of the disclosed inventions. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

I claim:

1. An apparatus for repairing a fractured humeral bone, comprising:
    a shoulder prosthesis having a shaft positionable within the medullary canal of a humeral bone, the shaft defining one or more holes; and
    a positioning jig for positioning the shoulder prosthesis at a desired height in the medullary canal, the positioning jig including
        a humeral engagement portion configured to engage the humeral bone,
        a prosthesis holder portion coupled to the humeral engagement portion such that the prosthesis holder portion engages and holds the shoulder prosthesis in the medullary canal at an adjustable height relative to the humeral bone while the humeral engagement portion is engaged with the humeral bone, and
        a targeting portion coupled to the prosthesis holder portion and configured to target one or more locations on the humeral bone corresponding to the one or more holes defined by the shaft of the shoulder prosthesis.

2. The apparatus of claim 1, wherein the humeral engagement portion is configured to engage an exposed portion of the humeral bone.

3. The apparatus of claim 1, wherein the targeting portion includes a drill guide configured to direct a drill toward the one or more locations corresponding to the one or more holes, so that a fastener may be inserted through the bone and at least one of the one or more holes.

4. The apparatus of claim 1, further comprising an adjustment portion coupling the humeral engagement portion to the prosthesis holder portion and being operative to drive translational motion of the prosthesis holder portion with respect to the humeral engagement portion such that the height changes.

5. The apparatus of claim 4, wherein the adjustment portion is configured to convert rotary motion of part of the adjustment portion into translational motion of the prosthesis holder portion.

6. The apparatus of claim 5, wherein the adjustment portion includes a handle configured to be grasped and turned by hand to drive the translational motion of the prosthesis holder portion.

7. The apparatus of claim 4, wherein the adjustment portion includes a threaded rod, and wherein the translational motion of the prosthesis holder portion is driven by rotation of the threaded rod.

8. An apparatus for repairing a fractured humeral bone, comprising:
    a shoulder prosthesis; and
    a positioning jig for positioning the shoulder prosthesis at a desired height in the medullary canal of the humeral bone, the positioning jig including
        a humeral engagement portion configured to engage the humeral bone,
        a prosthesis holder portion configured to engage and hold the shoulder prosthesis at a height in the medullary canal with the humeral engagement portion engaged with the humeral bone, and
        an adjustment portion coupling the humeral engagement portion to the prosthesis holder portion and configured to convert rotary motion of part of the adjustment portion into translational motion of the prosthesis holder portion with respect to the humeral engagement portion such that the height changes.

9. The apparatus of claim 8, wherein the adjustment portion includes a handle configured to be grasped and turned by hand to drive the translational motion of the prosthesis holder portion.

10. The apparatus of claim 8, wherein the adjustment portion includes a threaded rod, and wherein the translational motion of the prosthesis holder portion is driven by rotation of the threaded rod.

11. The apparatus of claim 8, wherein the shoulder prosthesis has a shaft positionable within the medullary canal of a humeral bone, and wherein the shaft defines one or more holes, further comprising a targeting portion coupled to the prosthesis holder portion and configured to target one or more locations on the humeral bone corresponding to the one or more holes defined by the shaft of the shoulder prosthesis.

* * * * *